United States Patent
Newman et al.

(10) Patent No.: US 6,617,151 B1
(45) Date of Patent: Sep. 9, 2003

(54) METHOD OF CLOSING A CELL CONTAINMENT DEVICE WITH A WET SEAL

(75) Inventors: Steven C. Newman, Flagstaff, AZ (US); Brian H. Kram, Flagstaff, AZ (US); Terry A Hubbard, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 09/515,264

(22) Filed: Feb. 29, 2000

(51) Int. Cl.$^7$ ............ C12M 1/00; C12M 3/00; C12N 5/00; C12N 1/00; A61F 2/00
(52) U.S. Cl. .......... 435/283.1; 424/93.4; 424/93.7; 424/424; 435/182; 435/243; 435/325; 435/293.1; 604/890.1
(58) Field of Search ............... 435/182, 243, 435/382, 325, 395, 283.1, 293.1; 424/424, 93.4, 93.7; 604/890.1, 891.1

(56) References Cited

U.S. PATENT DOCUMENTS

| | | |
|---|---|---|
| 3,953,566 A | 4/1976 | Gore ............ 264/288 |
| 4,187,390 A | 2/1980 | Gore ............ 174/202 R |
| 4,439,296 A | 3/1984 | Swarup ............ 204/253 |
| 4,774,001 A | 9/1988 | Degen et al. ............ 210/490 |
| 4,826,642 A | 5/1989 | Degen et al. |
| 5,366,631 A | 11/1994 | Adiletta |
| 5,373,620 A | 12/1994 | Zine |
| 5,387,237 A | 2/1995 | Fournier et al. |
| 5,476,589 A | 12/1995 | Bacino |
| 5,545,223 A | 8/1996 | Neuenfeldt et al. |
| 5,549,675 A | 8/1996 | Neuenfeldt et al. |
| 5,653,687 A | 8/1997 | Mills et al. |
| 5,653,688 A | 8/1997 | Mills et al. |
| 5,713,887 A | 2/1998 | Mills et al. |
| 5,738,673 A | 4/1998 | Mills et al. |
| 5,827,293 A | 10/1998 | Elliott |
| 5,843,069 A | 12/1998 | Butler et al. |
| 5,885,454 A | 3/1999 | Yagihashi et al. |
| 5,902,745 A | 5/1999 | Butler et al. |
| 5,913,998 A | 6/1999 | Butler et al. |
| 5,914,154 A | 6/1999 | Nemser |
| 5,919,330 A | 7/1999 | Pall et al. |
| 5,932,460 A | 8/1999 | Mills et al. |
| 5,935,370 A | 8/1999 | Weimer et al. |
| 5,964,261 A | 10/1999 | Neuenfeldt et al. |

*Primary Examiner*—David M. Naff
(74) *Attorney, Agent, or Firm*—Eric J. Sheets

(57) ABSTRACT

A method is provided for closing a containment device that involves wetting at least a portion of a permeable polymeric membrane such as tubular membrane with a liquid such as a cell suspension or drug formulation the device is being filled with, and applying heat to at least a portion of a wetted thermoplastic polymer in association with the membrane to form a "wet seal" closure. The thermoplastic polymer melts at a lower temperature than the polymeric membrane and the melted polymer integrates with the membrane by flowing along surfaces and into available interstices of the membrane to form a cell-tight closure when the polymer cools below its melt temperature. The application of heat may be accompanied by slight pressure, and a heat sink may be applied to limit heat transfer beyond the closure region to the membrane. In association with melting of the polymer, the membrane/thermoplastic polymer combination may be twisted and/or elongated, and twisting may form a separation region which can be cut to form first and second devices. The membrane and thermoplastic polymer may be made of polytetrafluoroethylene and fluorinated ethylene propylene, respectively. The containment device may be directly implanted into a recipient in need of a treatment provided by contents of the device.

29 Claims, 21 Drawing Sheets

METHOD OF CLOSING A CELL CONTAINMENT DEVICE WITH A WET SEAL

BACKGROUND OF THE INVENTION

1. Field of the Invention

The invention relates to the field of implantable devices and more particularly to devices that are wet or heat sealed.

2. Background Information

Within the field of implantable devices, it is known to provide permeable membrane structures for implantation, the structures configured to hold drug formulations or cellular suspensions. A number of techniques have been proposed to form those structures and seal the structures. In the majority of those known techniques, the device is manufactured without the cellular suspension or drug formulation. Subsequent loading of the cellular suspension or drug formulation may occur outside a host or after the device is implanted into the host.

When a suitable cell suspension or drug formulation is loaded into the device, it is typical and frequently desireable for the permeable membrane to become wet with fluid. Given the nature of the membranes, it is known that sealing a wet membrane can be difficult or impossible. This is because known glues and solvents that are appropriate for membranes in a dry state are frequently not compatible with a wet membrane, or are toxic to cell suspensions loaded into the membrane structure. To offset this difficulty, different dry and wet seal techniques have been proposed.

In one technique, such as disclosed in U.S. Pat. No. 5,902,745 to Butler et al., the device includes a permeable tubular membrane, which is sealed with a mechanical seal after loading the device with an appropriate cell suspension. In this technique, the membrane is wet when the seal is formed, but seal integrity relies on the quality of the mechanical seal. With implantable devices, the mechanical seal dimensions are small and can be difficult to reliably manipulate. In addition, because the loading and sealing operations can be distinct, there is an opportunity for contamination of the device exterior with cells from the cell suspension after the loading operation.

In another technique, such as disclosed in U.S. Pat. Nos. 5,653,687; 5,653,688; 5,713,887; 5,738,673 and 5,932,460 issued to Mills et al, a dry seal is formed after the device is loaded. However, the loading and sealing steps are distinct and the device is open to the loading environment after loading and before the device is sealed. For some of these seals, the seal depends on mechanical aspects of the seal. Some of the disclosed seal techniques require a solvent based seal. The solvents described may be toxic to the cell suspension, however. In one particular embodiment of the seal, a portion of the device is broken off and removed after loading and prior to sealing. This action presents a strong possibility of contaminating the loading environment. This contamination can be subsequently transferred to the exterior of the device, or to other devices or apparatus.

In another technique, such as disclosed in U.S. Pat. Nos. 5,545,223 and 5,549,675 issued to Neuenfeldt et al., the apparatus or device is first implanted in a host and then loaded with a cellular suspension in the host environment. In addition to problems that are described with wet sealing of the device, this technique is performed through an incision or injection port following implantation in the host, thereby exposing the device and the host to a risk of contamination.

The technique of Neuenfeldt et al. also requires a larger device to accommodate the distance between the cell suspension and the seal. This larger device also produces greater host trauma during implantation.

In some of the known techniques, the device or apparatus is loaded in an area that is remote from the host. In these methods, the loading process or apparatus provides opportunities for contamination from drug formulations or cell suspensions between the loading and the sealing steps.

As described, the methods available do not provide a secure and reliable closure system, that reduces the possibility of contamination during loading. In addition, the methods available do not provide a method to reliably seal a device after the membrane is wet. Systems and methods to address these and other deficiencies are needed.

SUMMARY OF THE INVENTION

In one aspect, the present invention provides a method of closing a containment device that comprises wetting at least a portion of a permeable polymeric membrane of the containment device with a liquid and applying heat to at least a portion of a wetted thermoplastic polymer in association with the membrane to create a closure. Such a closure is referred to herein as a "wet seal." In this "wet sealing" process, the thermoplastic polymer melts at a lower temperature than the polymeric membrane. Once melted, the thermoplastic polymer integrates with the polymeric membrane and flows along surfaces and into available interstices of the membrane. Through passageways become filled with the melted polymer, thereby blocking fluid communication in the polymeric membrane in the region of the closure. When the thermoplastic polymer cools below its melt temperature, a closure is formed in the device. The closure is cell-tight and often liquid-tight. The portion of the device having a closure formed with a wet seal delineates a cell-impermeable region of the device.

The application of heat may be accompanied by slight pressure and a heat sink may be applied to limit heat transfer beyond the closure region to the permeable membrane. After forming the closure, the method may include pressure checking the closure integrity. The device may include additional closures that are formed by wet or dry sealing techniques.

In one aspect, the present invention provides a method of closing a containment device that comprises wetting a porous expanded polytetrafluoroethylene (ePTFE) membrane of the containment device with a liquid, and applying heat to a portion of the membrane in communication with a thermoplastic polymer, such as fluorinated ethylene propylene (FEP), to create a closure. The closure is formed by melting and fusing of the polymer to itself and the membrane in the presence of the liquid.

In one aspect, the present invention provides a method of closing a containment device comprising wetting a permeable membrane of the containment device with a liquid, wetting a thermoplastic polymer region of the device with the liquid and applying heat directly to the thermoplastic polymer region to create a closure. In this aspect, the thermoplastic polymer region is joined to the permeable membrane before wet sealing the containment device.

In one aspect, the present invention provides a method of closing a containment device that comprises applying sufficient heat to a portion of a permeable membrane in association with a thermoplastic polymer to melt and flow the thermoplastic polymer, followed by twisting the membrane/thermoplastic polymer combination in the region of the heating to form a closure. The membrane/thermoplastic polymer combination is also elongated while heating or twisting the materials. After heating, twisting, and elongation a separation region is formed and the membrane is cut in the separation region.

In one aspect, the present invention provides a containment device comprising a membrane, a polymer in communication with the membrane, and a closure. The closure is created by applying heat to a portion of the membrane and a portion of the polymer after wetting the membrane with a liquid.

In one aspect, the present invention provides a containment device comprising a membrane, a polymer region joined to the membrane and a closure. The closure is created by applying heat directly to the polymer region after wetting the membrane and the polymer region with a liquid.

In one aspect, the present invention provides a containment device comprising a membrane and a closure. The closure is created by applying heat to a portion of the membrane and twisting the membrane in the region of the heating.

In one aspect, the present invention provides a method of forming a containment device. The method comprises forming a containment region that includes a membrane, forming a thermoplastic polymer region joined to the membrane and forming a closure region. The closure region communicates with the containment region and applying heat directly to the thermoplastic polymer region after wetting the membrane creates a closure in the closure region.

In one aspect, the present invention provides a method of forming a containment device. The method comprises forming a containment region that includes a membrane, and forming a closure region. The closure region communicates with the containment region and applying heat to a portion of the membrane and twisting the membrane in the region of the heating creates a closure in the closure region.

In one aspect, the present invention provides a method of loading a containment device comprising placing a cell suspension or drug formulation in a containment region of the device through a closeable opening, the containment region including a membrane and the liquid wetting the membrane, and creating a closure in the closeable opening by applying heat to a portion of the membrane in association with a thermoplastic polymer.

In one aspect, the present invention provides a method of loading a containment device comprising creating a closed cell-tight system, the system including the containment device and a source of metabolically active cells. Loading a containment region of the device with the metabolically active cells via a closure region, the containment region including a membrane. Creating a closure at the closure region, the closure substantially or completely eliminating metabolically active cells in the vicinity of the closure, and subsequent separation of the source of cells while maintaining a closed cell-tight system.

The foregoing specific aspects, objects and advantages of the invention are illustrative of those which can be achieved by the present invention and are not intended to be exhaustive or limiting of the possible advantages that can be realized. Thus, the aspects, objects and advantages of this invention will be apparent from the description herein or can be learned from practicing the invention, both as embodied herein or as modified in view of any variations which may be apparent to those skilled in the art. Accordingly the present invention resides in the novel parts, constructions, arrangements, combinations and improvements herein shown and described.

BRIEF DESCRIPTION OF THE DRAWINGS

The foregoing features and other aspects of the invention are explained in the following description taken in conjunction with the accompanying figures wherein.

It is understood that the drawings are for illustration only and are not limiting. It is specifically understood that the scale of elements and relative dimensions in the drawings may be exaggerated to provide clarity and illustrate individual aspects.

DETAILED DESCRIPTION OF THE INVENTION

The invention provides a containment device, methods of making the device and methods of loading and sealing the device. The containment device is particularly suited for use as a medical device, such as a cell encapsulation device, a drug delivery device, or a gene therapy device. The containment device may be inserted into a previously implanted containment apparatus residing within a recipient, such as an animal or human, or it may be implanted directly in a recipient. The device includes a permeable membrane, which partially defines an enclosed space of the device, and a closure region of the device. Materials (e.g., cells, or drugs) are loaded into the device from a loading device through the closure region into a containment region, after which the closure region is treated to form a closure. The closure is typically created by heating a thermoplastic polymer associated with the permeable membrane in the presence of a liquid that wets at least a portion of the membrane in the closure region. The liquid may also wet at least a portion of the thermoplastic polymer. Wetting of the membrane is often a result of filling the device with a liquid, such as a cell suspension or drug formulation, or from sterilization procedure prior to filling. Forming the closure may include pressure or clamping as part of the sealing process. A closure formed in this manner is referred to herein as a "wet seal."

Different embodiments for creating the closure after loading the containment device are disclosed. In one embodiment, the closure is created when heat is applied to a portion of a tubular porous expanded polytetrafluoroethylene (ePTFE) membrane, which includes a tube of fluorinated ethylene propylene (FEP) thermoplastic polymer in association with the ePTFE membrane. The applied heat is sufficient to melt the FEP thermoplastic, but not of a magnitude to melt or substantially degrade the ePTFE membrane. While the FEP is in a melted state, the tubular membrane in the region of the melted FEP is pressed together, preferably by twisting the tubular device around its longitudinal axis, and elongated, thereby creating the closure. In effect, the FEP and ePTFE form a fused or welded cell-free and cell-tight wet seal closure. After forming the wet seal closure, the containment device is separated from the cell loading device by a cut through the fused ePTFE/FEP material in the closure region.

Figure 22:
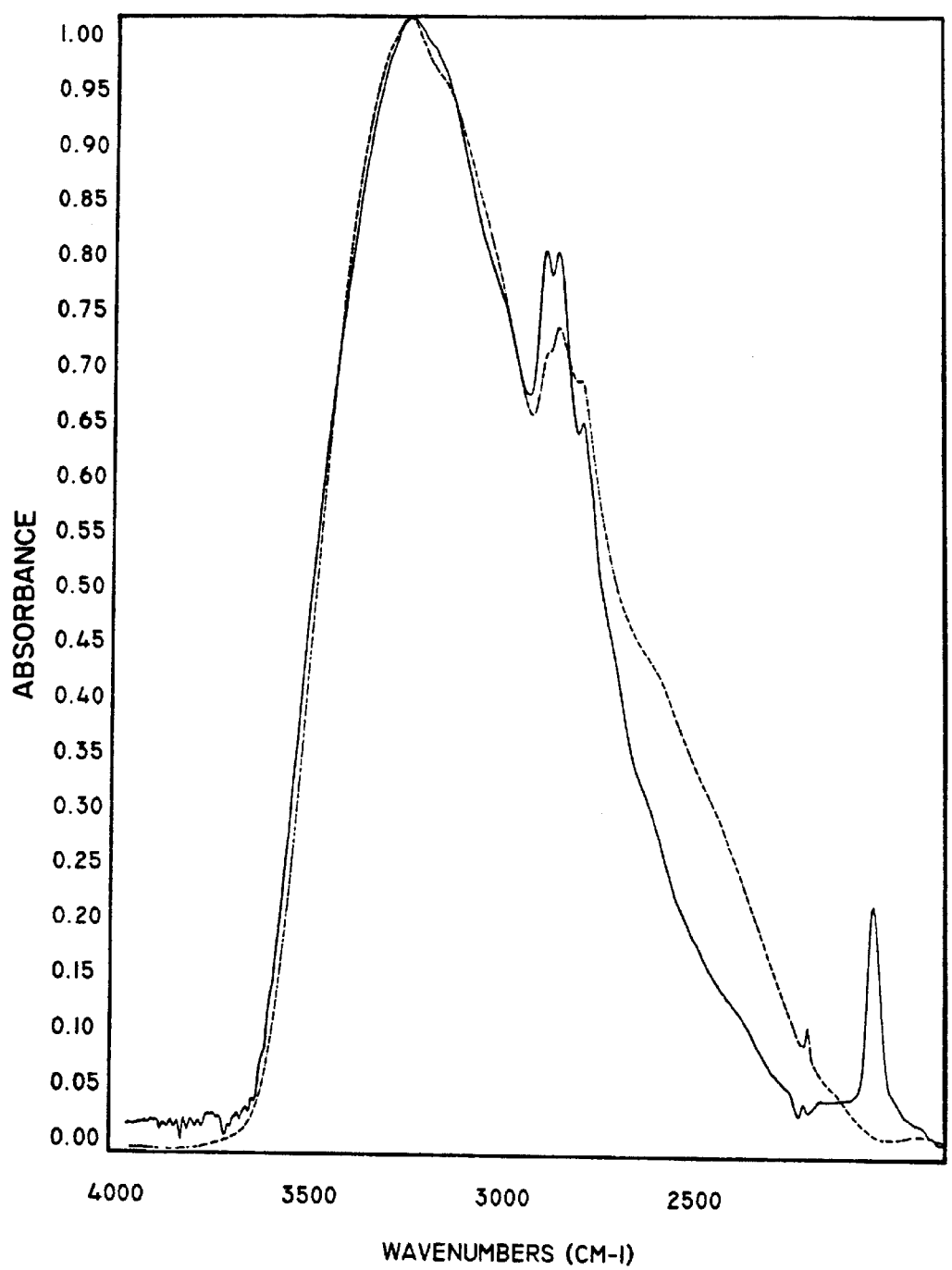
FIG. 22 is a graph showing the presence of chemical groups from residue associated with wet seals of the instant invention.

After a wet seal is formed, thermally degraded residue from cells or cell culture media can usually be found on surfaces of material in the closure region. Residue may also be embedded in material of the closure region. The presence of such residue can be detected by sampling charred material from the closure region and subjecting the sample and a control to analysis. A preferred analytical method is Fourier Transform Infrared Spectroscopy (FTIR). In comparison with a control, chemical groups indicating degradation of cells or cell culture media in the wet seal region become evident as changes in peaks on a graph. An example of such a graph is shown in FIG. 22. In the graph, the curve represented by a dotted line is from a control sample. The curve represented by a continuous line are peaks generated from a test sample. Differences in the peaks on the graph are indicative of chemical changes in the cell culture media used to load cells into a device of the present invention at the time of a thermally effective wet sealing process in the closure region. Such residue is only present in the closure region if a wet seal has been formed in the region.

Another important aspect of the invention is that the containment device and the loading device form a closed cell-tight system during loading, sealing and separation. This closed cell-tight aspect of the system is maintained during the loading and closure or sealing and subsequent separation of the containment device. In this manner, contamination of the device exterior by cells from either the loaded device or the cell delivery device is completely or substantially prevented.

During trials, containment devices were manufactured, loaded, sealed and later implanted according to the instant invention. These tests positively demonstrate that the methods and apparatus disclosed in the instant application accomplish the stated objectives of reducing or eliminating contamination of the device exterior and containing cells within the device. In vitro testing demonstrated that exterior contamination during device loading was reduced or eliminated by using the disclosed method and system. In vivo testing for up to 6 months showed that cell containment within the containment device was possible without device or seal failure. These test results provide strong evidence that containment devices, manufactured, loaded, sealed and implanted according to the instant invention, will maintain the desired isolation of cells within the device.

Another important aspect of the invention is that forming the closure through clamping or pressure does not compromise the mechanical integrity of the containment device.

Uses or Applications of the Device

The containment device according to the instant invention can be directly implanted in a recipient in need of treatments provided by the contents of the device. When directly implanted in a recipient, known surgical techniques are used to prepare an implantation site and position the containment device in the recipient. This includes an incision at the site and preparation of a tissue envelope to hold the containment device. For ease of insertion, incisions may be used to allow threading of the containment device between the incisions. The implantation site can be a subcutaneous location that is somewhat protected from external forces and not subject to significant flex during normal recipient activities. As examples, the inner forearm or the inner upper thigh of a human may be appropriate sites.

Figure 1:
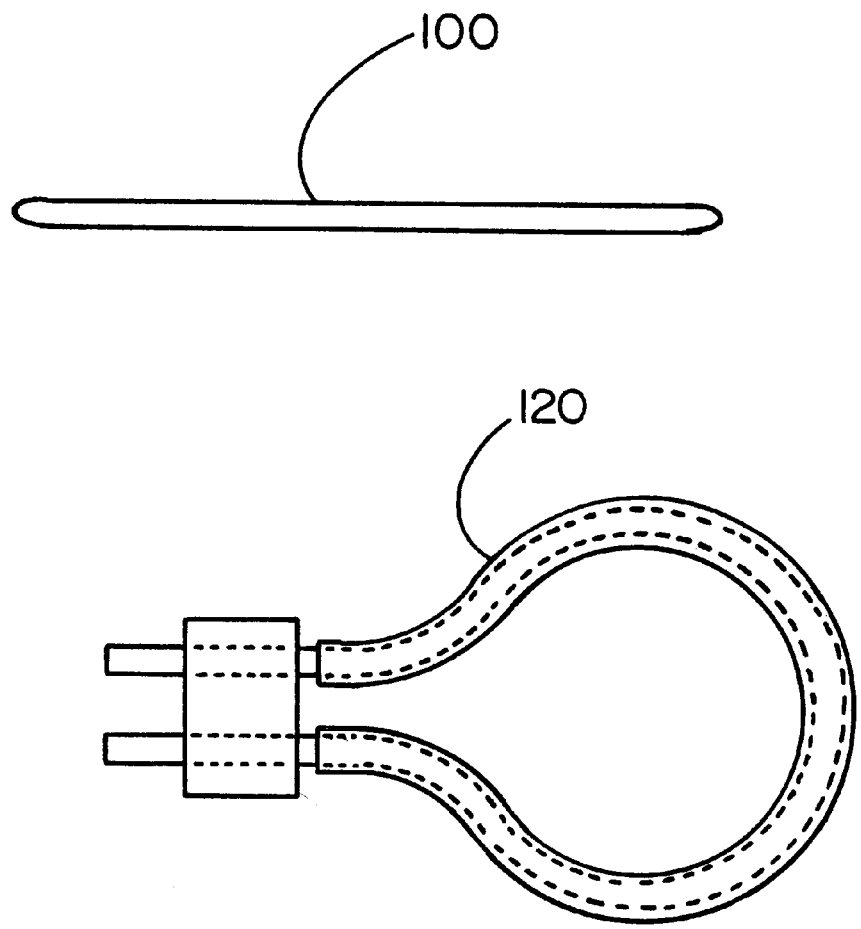
FIG. 1 illustrates a containment device of the instant invention and an implantable containment apparatus suitable for holding the containment device.

The containment device can also be indirectly implanted in a recipient with the used of a containment apparatus for the device. Such an apparatus is disclosed in U.S. Pat. No. 5,843,069, issued to Butler et al. (the '069 patent) and incorporated herein by reference. Referring to FIG. 1, the containment device 100 according to the instant invention can also be placed or replaced in an implantable containment apparatus 120 of the '069 patent. The apparatus and methods disclosed in the '069 patent overcome some of the above-described problems with direct implantation.

When the containment device 100 of the instant invention is used with the implantable containment apparatus 120 of the '069 patent, the containment device is first prepared or filled with the appropriate cell suspension or drug formulation. After prepared or filled, the containment device is wet sealed, as described in greater detail below. Once wet sealed, the containment device is placed or replaced in the implantable containment device of the '069 patent.

In a preferred embodiment, the containment device provides a sealed environment for cellular suspensions or drug formulations. However, the device has other embodiments and applications where a permeable membrane encloses a space and the device is placed within a host or recipient. For example, as micro-machining techniques become more common, it will be appropriate for the containment device 100 to contain a micro-miniature factory, the factory providing different forms of processing. In this embodiment, the factory performs any number of different manufacturing functions. These include neutralizing or changing the composition of molecules, substances or compounds in the recipient. The micro-miniature factory within the containment device of the instant invention can also produce drugs or compounds that are harvested from the host or recipient. The factory is passive, such as a catalyst, or it is active, with a power source such as internal metabolism of proteins from the nutrient, or external power from outside the host or recipient. In short, the invention does not envision limiting the materials within the containment device to only cell suspensions or drug formulations.

Materials for the Membrane of the Present Invention

The containment device of the instant invention includes a permeable membrane. Preferred permeable membranes are much like the permeable membrane of the '069 patent's implantable containment apparatus. The membrane of the instant invention allows transport of nutrients, cellular wastes, and other materials through and across the membrane, but the membrane prevents cell movement or migration through and across the membrane.

Figure 2:
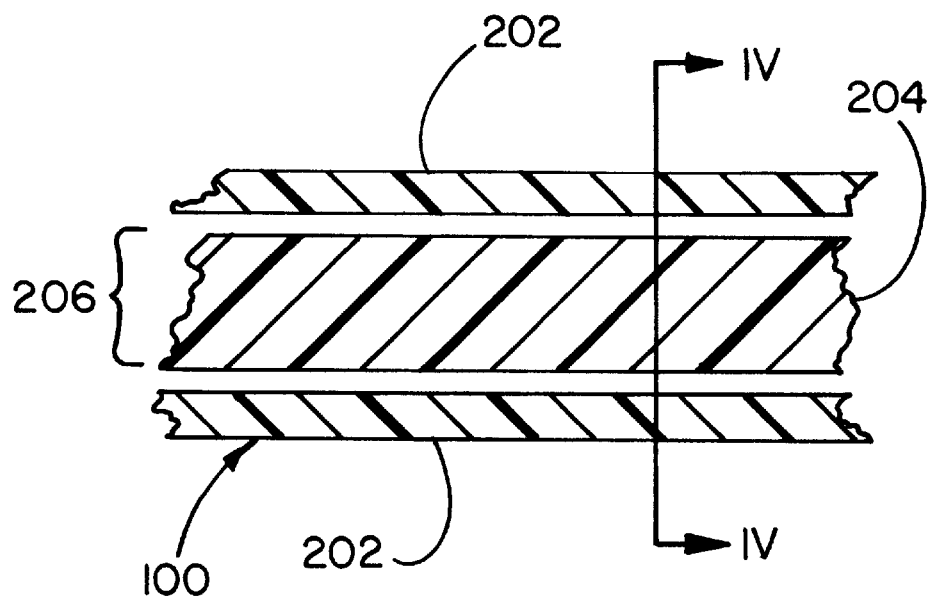
FIG. 2 illustrates a cross-section of an embodiment of the containment device of the instant invention.

Referring to FIG. 2, the exterior tube 202 of containment device 100 of the present invention is made, primarily, of a permeable polymeric material having sieving properties. The sieving properties of such permeable polymeric materials can be adjusted to control passage of solutes, biochemical substances, viruses, or cells, for example, through the material, primarily on the basis of size. Preferred permeable polymeric materials in the present invention are porous. In general, as the average pore size of a porous polymeric material increases, increasingly larger biochemicals and biological entities are able to pass through the material. In the present invention, porous polymeric materials capable of preventing the passage of biological cells through the material, while permitting biological molecules to pass through the material, are most preferred.

Porous polymeric materials suitable for construction of the exterior tube 202 of a containment device of the present invention include, but are not limited to, porous expanded polytetrafluoroethylene (ePTFE); porous polypropylenes (PP), such as CELGARD (Celanese Separations, Inc., Charlotte, N.C.), SOLVEX (Millipore Corporation, Bedford, Mass.), and METRICEL (Gelman Sciences, Ann Arbor, Mich.); porous polyethylene (PE), including stretched and sintered forms; porous polyvinylidene fluoride or PVDF (e.g., DURAPORE, Millipore Corporation, Bedford, Mass., or FP VERICEL, Gelman Sciences, Ann Arbor, Mich.); track-etched and other porous polycarbonates (e.g., ISOPORE, Millipore Corporation, Bedford, Mass.); woven or non-woven collections of fibers or yarns, or fibrous matrices, such as those described by Fournier et al. in U.S. Pat. No. 5,387,237 (incorporated herein by reference); or foams of polyvinyl alcohol (PVA), polypropylene (PP), or polyethylene (PE), either alone or in combination.

Other materials suitable for construction of exterior tube 202 include polymers such as biocompatible polyamides (FH-66, Gambro A B, Lund, Sweden); cellulosics such as cellulose acetate, nitrocellulose, and mixtures thereof (e.g., N C, Schleicher and Schuell, Inc., Keene, N H, and M F, Millipore Corporation, Bedford, Mass., or METRICEL, Gelman Sciences, Ann Arbor, Mich.); polyacrylamide and its copolymers with acrylic acid and acrylonitrile (e.g., HYPAN, Hymedix, Inc., Dayton, N.J.); polyacrylonitrile or PAN and its copolymers, including with sodium methallysulfonate (AN-69, Hospal, Lyon, France) and poly (acrylonitrile-co-vinyl chloride) or (PAN-PVC); porous poly (ether ether ketones) or PEEKs; porous polysulfones including poly (ether sulfones) or PESs (e.g., TUFFRYN or SUPOR, Gelman Sciences, Ann Arbor, Mich.); or stable, strong, biocompatible hydrogels used in soft contact lenses, such as poly (2-hydroxyethyl methacrylate) or polyHEMA, poly(N-vinyl-2-pyrrolidone) or PVP, and mixtures and copolymers thereof.

Expanded, porous polytetrafluoroethylene is preferred for construction of tube 202. Porous expanded polytetrafluoroethylene (ePTFE) is characterized as a material having void spaces defined by nodes and fibrils. Methods for making ePTFE are taught by Gore in U.S. Pat. Nos. 3,953,566 and 4,187,390, each of which is incorporated herein by reference. However, the methods for making ePTFE are not subjects of the present invention.

For ePTFE, or similar fibrillated material, the pore size is related to the fibril length and fibril density of the material and the thickness of the material. In the present invention, appropriate ePTFE materials are selected that resist cellular movement across the thickness of the material, while being selectively permeable to macromolecules. These materials have microstructures (i.e., fibril length and fibril density) in combination with material thickness control in large part the sieving properties, or permeability, of the membrane material. Another approach to characterize the sieving properties of a porous materials, such as ePTFE, is to measure resistance to fluid flow across the materials. One appropriate measure is the pressure at which a gas can pass through the porous material and form bubbles when the material is immersed in an appropriate liquid. This measurement technique is referred to as a "bubble point" metric.

Method of Making the Device

Figure 4:
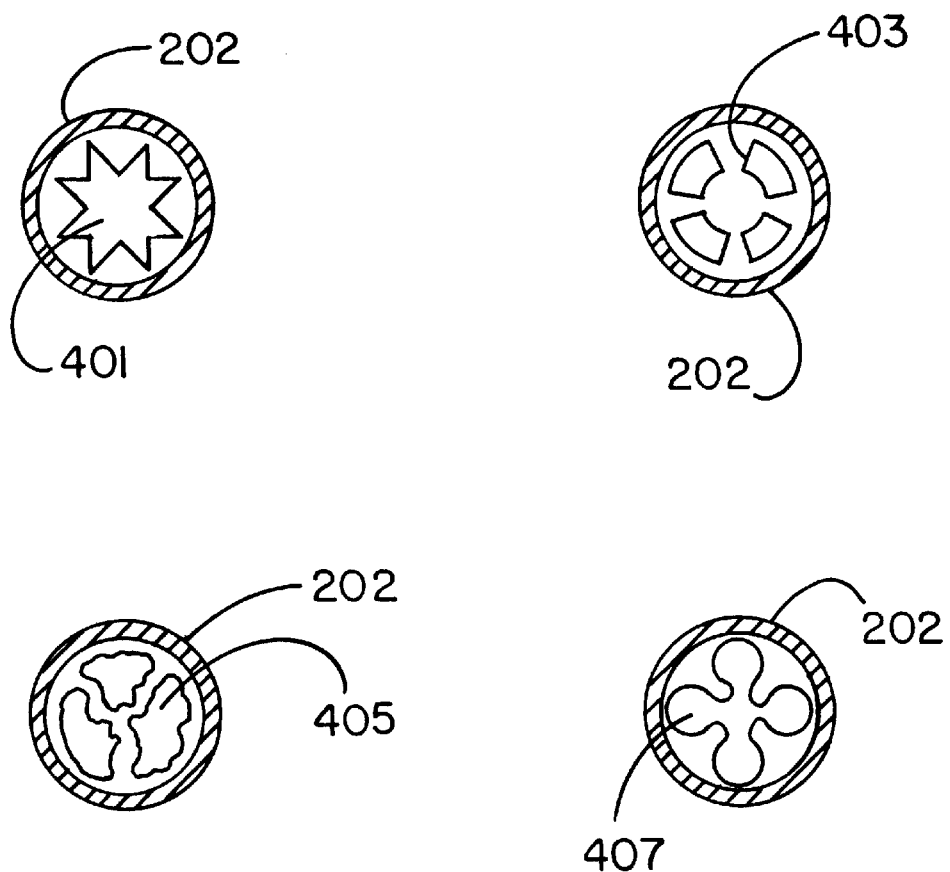
FIG. 4 illustrates various cross-section embodiments of the containment device of the instant invention.

Referring to FIG. 2, in a preferred embodiment, a containment device 100 of the present invention is in the form of a tube. The tube walls create a central lumen 206, which can hold a drug formulation, cell suspension, or other agent. In a preferred embodiment with a cell suspension, lumen 206 surrounds a central core 204, which can have a number of cross-sectional shapes. Examples of the various cross-sectional shapes are illustrated in FIG. 4, with a star shape 401, a perforated cylinder 403, a randomly porous matrix 405 and a bulb extrusion 407.

The tube walls 202 are made of a membrane, which comprises an ePTFE material. The membrane is a layer of ePTFE material that is a very thin, very strong non-woven web composed substantially of tightly spaced fibrils in which there are essentially no nodes. The fibril lengths have average dimensions ranging between about 0.2 and about 4.0 microns, as measured by photomicrography. The fibril density is observed to be very high and tightly packed with multiple points of contact. The points of contact do not have sufficient polytetrafluoroethylene material to be referred to as nodes. The thickness of the material in its finished form is between about 1 micron and about 25 microns. The preferred method of making the membrane utilizes a portion of a method taught by Bacino in U.S. Pat. No. 5,476,589 entitled "Porous PTFE Film And A Manufacturing Method Therefor," which is incorporated herein by reference.

Figure 3:
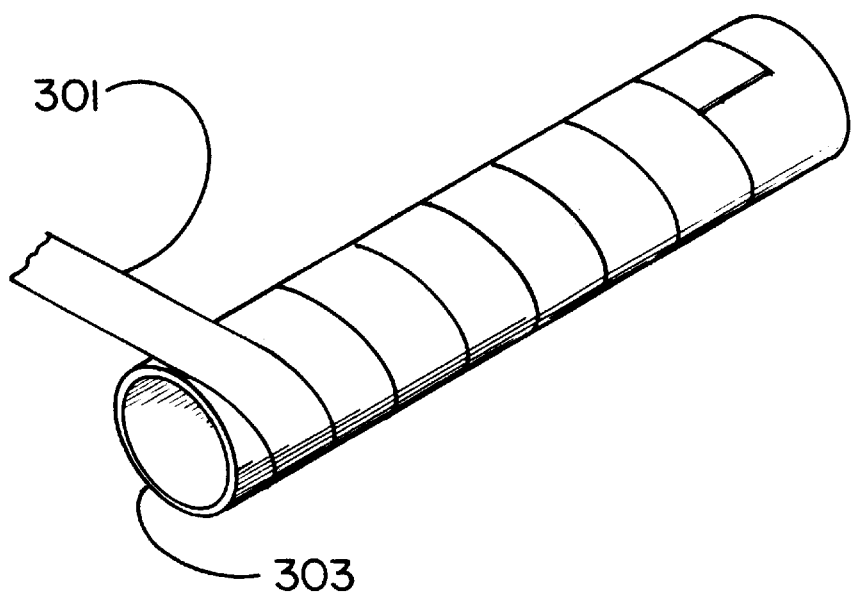
FIG. 3 illustrates an embodiment to form the tubular membrane of the instant invention.

Referring to FIG. 3, a preferred method to form a containment device of the present invention in a tubular shape is by wrapping the ePTFE membrane 301, made in accordance with the teachings of Bacino, on a mandrel 303. Longitudinal and helical orientations of the wrapped film may be used. A single layer or multiple layers of wrapped film may be employed. The wraps may be set so as to overlap, or to gap, depending on the setting of such variables as film width, wrap angle, and mandrel diameter. In many applications, the overlap is preferably about 50%. This construction is then heated from about 340° C. to about 400° C., preferably 385° C., for about 5–10 minutes to bond the respective layers to each other.

Another way to form an ePTFE containment device of the present invention is through direction extrusion and expansion of the membrane as a tube. However, the various methods to form a tubular membrane are not key aspects of the invention.

A tubular ePTFE membrane, formed as described above, is a hydrophobic membrane. Accordingly, the membrane does not readily permit liquid water to enter and traverse the void or porous spaces and passages of the membrane. It is known to apply certain alcohols, low surface tension liquids, wetting agents or surfactants to the ePTFE to render the membrane wettable with liquid water. These methods are described in U.S. Pat. No. 5,902,745 to Butler et al., the disclosure of which is incorporated herein by reference. However, methods to form a wettable membrane are not subjects of the present invention.

In a preferred embodiment, the membrane is treated to make it wettable. In this embodiment a very dilute aqueous solution of a wetting agent, such as polyvinyl alcohol (PVA) is used. For example, 0.001% polyvinyl alcohol in saline (weight to volume or w/v) provides enough wetting agent to the ePTFE material to prevent, or limit, spontaneous dewetting of the material. This also prevents, or limits, evolution of air bubbles in a containment device loaded with cells. The PVA also renders the normally opaque ePTFE material essentially translucent to transparent upon wetting. Suitable wetting agents and/or surfactants for use in this method include, but are not limited to, polyvinyl alcohol, polyethylene glycol, sodium dodecyl sulfate, fluorosurfactants, pluronics, and bile salts in percentages ranging from about 0.001–5.0%. Suitable solvents for this method include, but are not limited to, saline, water, and aqueous buffers, for example.

In the preferred embodiment of the present invention, wetting agents and/or surfactants are adsorbed onto the surfaces and into the void spaces, pores, or passages of the ePTFE membrane and preferably immobilized in situ in order to make the ePTFE material wettable with liquid water. There are many ways to immobilize wetting agents or surfactants, such as, cross-linking, substrate grafting, plasma immobilization, ionic complexation, and free radical grafting, etc. In one example, cross-linking the adsorbed wetting agent or surfactant on the ePTFE in situ immobilizes the wetting agent or surfactant on the ePTFE material. Certain wetting agents or surfactants can be used that render ePTFE spontaneously and substantially completely liquid water wettable. A spontaneously and substantially completely water wettable ePTFE material permits liquid water to flow along the surface and through the passages of the material by merely contacting the material with liquid water. Suitable wetting agents or surfactants for use in the present invention include, but are not limited, to polyvinyl alcohol, poly(tetrafluoroethylene-co-vinyl alcohol), polyacrylic acid, polyethylenimine, and polyethylene glycol. Wetting agents and/or surfactants are adsorbed in various ways, such as solution, or neat, adsorption, vapor deposition, plasma immobilization, and thin film assembly, for example. Preferably, polyvinyl alcohol is adsorbed to ePTFE by adsorbing the polyvinyl alcohol onto the surfaces and into the porous, or void, spaces of the material, followed by immobilization via cross-linking the polyvinyl alcohol to itself with a dialdehyde such as glutaraldehyde.

A membrane of the present invention made of water wettable ePTFE is strong enough to withstand hydrostatic pressures sufficient to cause water to be forced through the pores of the material across the thickness of the membrane. When water is being forced across the thickness of the membrane, the water wettable ePTFE material functions as a filter, or an ultrafilter, depending on the permeability of the material. As water moves, or seeps, across the thickness of the membrane, it tends to collect into droplets on the outer surface of the membrane. As adjacent droplets grow in size, they merge and run off of the cover. This process is referred to herein as "weeping." Most water wettable membranes of the present invention are sufficiently permeable to water for pressurized water to visibly weep from the membrane without gross channeling of water.

Ideally, the membrane of the present invention is sufficiently water permeable to allow the ready separation of aqueous fluid from cells under relatively low pressure. A ready weep flow of ranging from about 0.01 ml/cm$^2$/minute to about 100 ml/cm$^2$/minute at a pressure ranging from less than about $3.4*10^4$ Pa to about $6.9*10^5$ Pa should permit relatively rapid cell concentration within the device.

This is an extremely beneficial attribute of the present invention. Unlike other cell containment devices that require cell concentration before insertion of the cells in the cell device and then carefully calculated and controlled transfer, the present invention allows cells to be easily transferred to any desired concentration with minimal pre-concentration steps. Further, by flushing a cell-filled apparatus after initial loading of the cells, a user can assure that all cells are flushed into the device and not left as a wasted residue on the apparatus.

Another benefit of the membrane becoming essentially translucent to transparent is that in a translucent or transparent condition, the cells in the device can be observed through the cover both during and after loading of cells. This not only assists in the loading of cells, but also makes monitoring of the cells during use much easier. Additionally, position of various elements of the containment device are more visible during assembly when the membrane is translucent.

In addition to using cells suspended in aqueous fluids in the present invention, cells suspended in viscous fluids, such as alginate, can also be loaded into the invention. With these cell suspensions, much less fluid weeps through the permeable membrane as the suspension is loaded in the device. This often requires the cell suspension to be more precisely characterized in terms of cells numbers than with the aqueous fluids described above. Islets of Langerhans are examples of cell types that often benefit from being suspended in a viscous fluid when used in the present invention.

The permeable membrane of the present invention should prevent cells from moving into or out or the device, but allow the passage of nutrients, waste products, and bioactive substances secreted by cells contained within the device. In one embodiment, the membrane excludes particles on a molecular scale. Such molecular weight cut off (MWCO) properties may be useful for excluding proteins, etc., produced by the immune system of a recipient from traversing the membrane that would adversely effect cells encapsulated in the device. The precise MWCO range appropriate for a particular application will vary depending on the membrane material, type of cells contained within the device, the size of the therapeutic cell product to be released into the surrounding environment, and the host environment, etc. Accordingly, selectively permeable membranes having a MWCO of between about 10 kD to about 2000 kD may be suitable for use in the present invention. A MWCO range of between about 30 kD and 150 kD is particularly preferred in applications where it is desired to isolate the contained cells from contact with molecules of the immune system capable of recognizing or destroying the contained cells.

Figure 5:
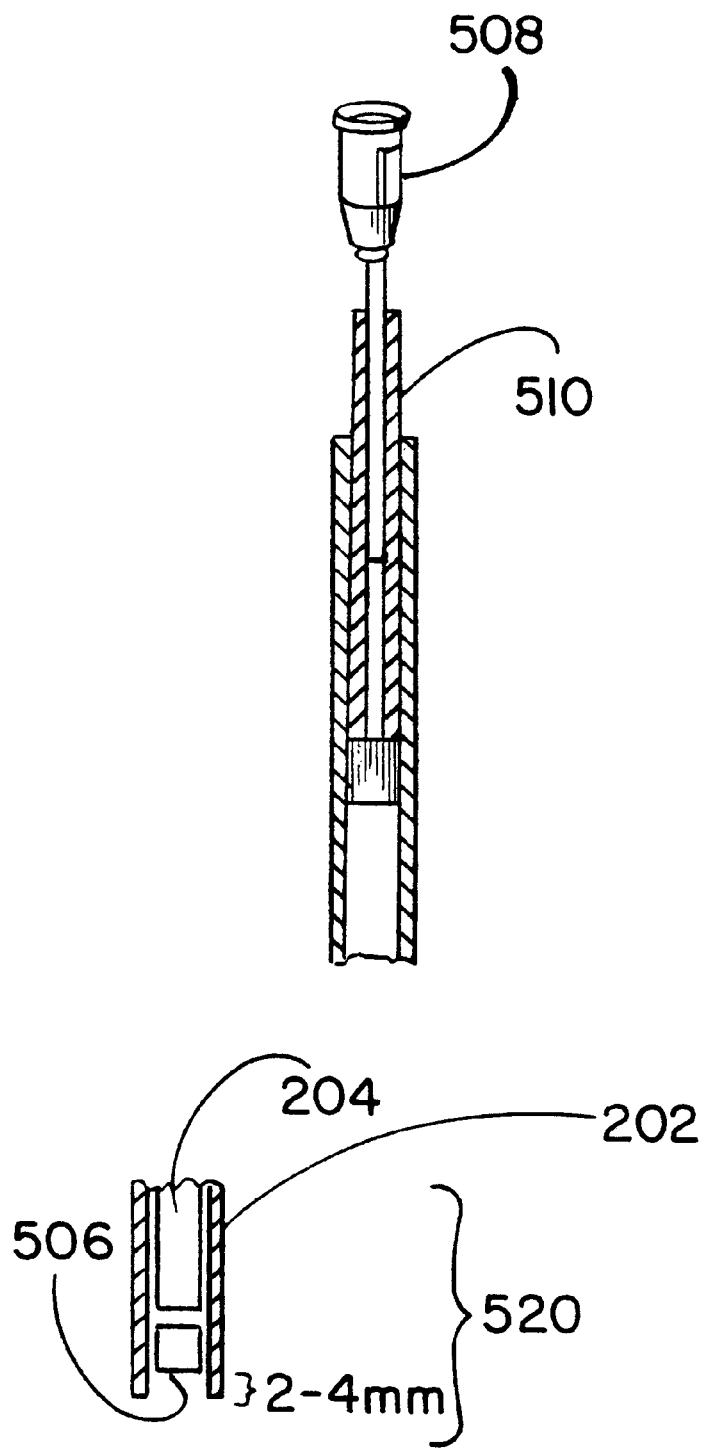
FIG. 5 illustrates an embodiment of the containment device of the instant invention.

Referring now to FIG. 5, a preferred method of making a containment device is as follows. This description is particularly appropriate for a device that will carry a cellular suspension. A central core 204 is placed within a tubular membrane 202. The core is a biologically inert material, such as silicone, and has a cross-sectional shape that is appropriate for the cell suspension. Examples of the cross-sectional shapes that are appropriate for a cell suspension are provided in FIG. 4. In a preferred embodiment, the core has a stellar cross-section 401. However, the cross-sectional shape of the core is not critical to the instant invention and may be any of a number of different shapes, such as those shown in FIG. 4. The core 204 length is only slightly shorter that the length of a finished containment device. The tubular membrane 202 is longer than the core 204 to allow closure of the membrane at one end and attachment of a loading device at the opposite end of the membrane. In this embodiment, the core is not attached to the membrane in the final device. In other embodiments, the central core is attached to the membrane in the closure region.

Figure 6:
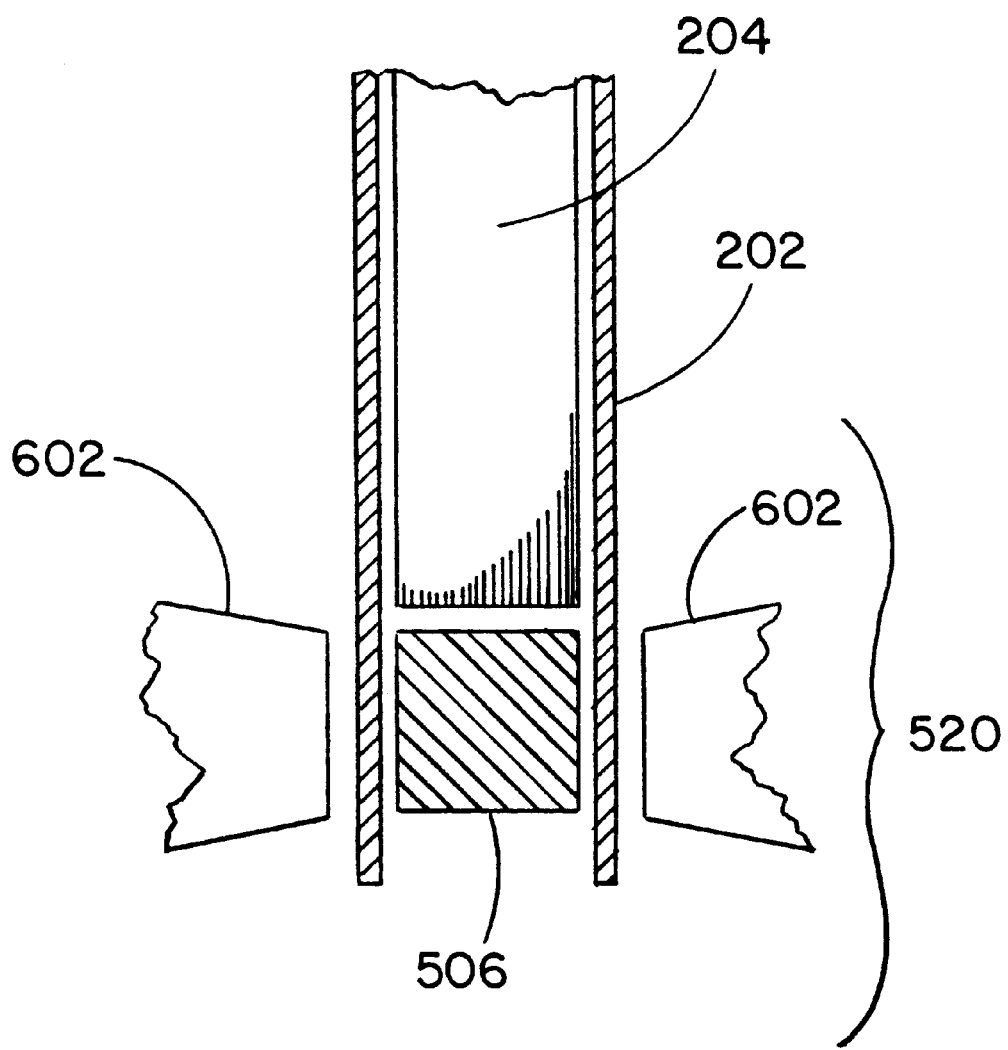
FIG. 6 illustrates an embodiment of a dry seal on an end of the containment device of the instant invention.

Referring to FIG. 6, after core 204 is placed within the tubular membrane 202, a polymer plug 506 is placed in one end of the tubular membrane, abutting core 204. In a preferred embodiment, plug 506 is fluorinated ethylene propylene (FEP). The core, plug and membrane are arranged so that approximately 2 mm of membrane 202 extends beyond the FEP plug and the FEP plug abuts the silicone core. In this arrangement, a heat source or implement 602 is applied to the membrane in the vicinity of the FEP plug. The temperature of heat source 602 is typically between 350° C. and 450° C., preferably 390° C., which is above the melt point of the FEP and causes the FEP to melt and flow. The temperature of the heat source is also slightly above the melt point of the ePTFE membrane. However, the heat exposure is not so great to cause any significant degradation or damage to the ePTFE membrane. As a result the membrane combines with the FEP plug to form a closure or seal 520 at the distal end of the containment device. For purposes of distinguishing different seals of the containment device, this seal will be termed a dry seal. In one embodiment, the opening in heat source 602 is slightly smaller than the diameter of FEP plug 506. In this embodiment, when heat source 602 is applied, a slight clamping pressure helps to form dry seal 520.

After cooling, this closure or seal 520 is substantially or completely impermeable to cells that are eventually loaded in the device. The closure is also generally impermeable to liquids within the device. This closure is considered to be a dry seal, because it is created by a dry seal technique. In this context, the closure technique is dry because the ePTFE membrane, the silicone core in the vicinity of the closure region, and the FEP plug are dry when the closure is created (i.e., aqueous fluids are absent during the formation of the closure).

Figure 7:
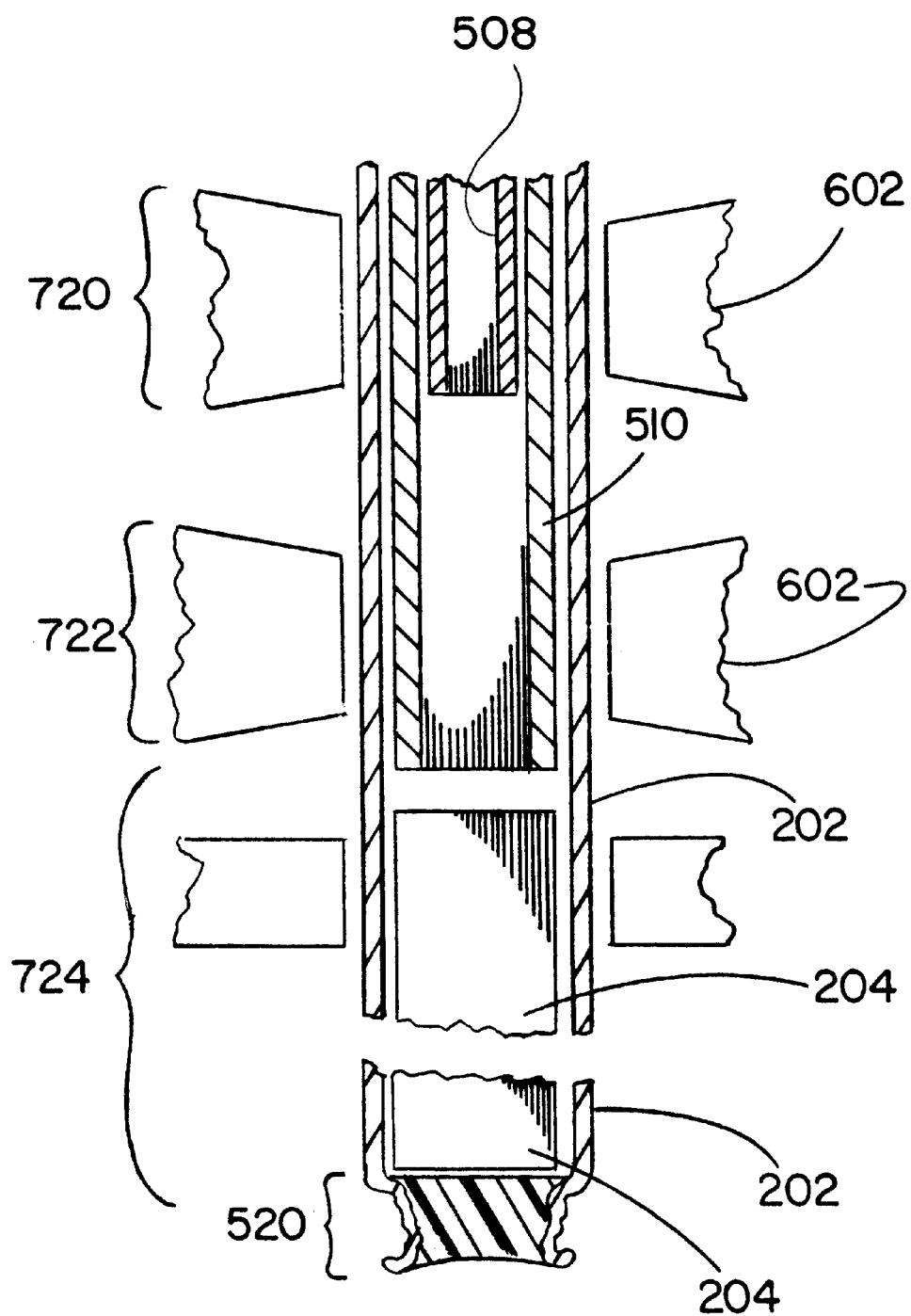
FIG. 7 illustrates a cross-section of an embodiment of the containment device of the instant invention.

Referring to FIGS. 5 and 7, after forming the dry closure on one end of the containment device, a blunt tip, such as an 18 gage needle 508 about 25 mm long is inserted into a tube 510 of a colored thermoplastic material. In a preferred embodiment, the tube is a colored thermoplastic material made of FEP about 25 mm long. Needle 508 and FEP tube 510 assembly are inserted into the proximal end of the tubular ePTFE membrane 202 that is opposite the dry seal 520.

The needle 508 and FEP 510 tube are advanced within the ePTFE membrane 202 until there is a slight gap of about 2 mm between the end of the FEP tube 510 and the silicone core 204. This slight gap is important for the subsequent wet loading and sealing of the containment device. At the same time, the silicone core 204 abuts the closure 520 at the other end. In this arrangement, heat source 602 is applied to the end of the membrane 202 with a slight clamping pressure where it bonds or seals the membrane to the FEP tube 510 and also bonds or seals the FEP tube to the needle 508. The colored FEP becomes visible through the membrane after removing the heat and allowing the seal to cool. This helps to visually confirm a cell impermeable seal. Referring to FIG. 7, a seal 720 is formed when the ePTFE membrane, FEP tube, and needle are dry. Therefore, it is formed by a dry seal technique and is a dry seal.

Figures 7A, 7B, 7C:
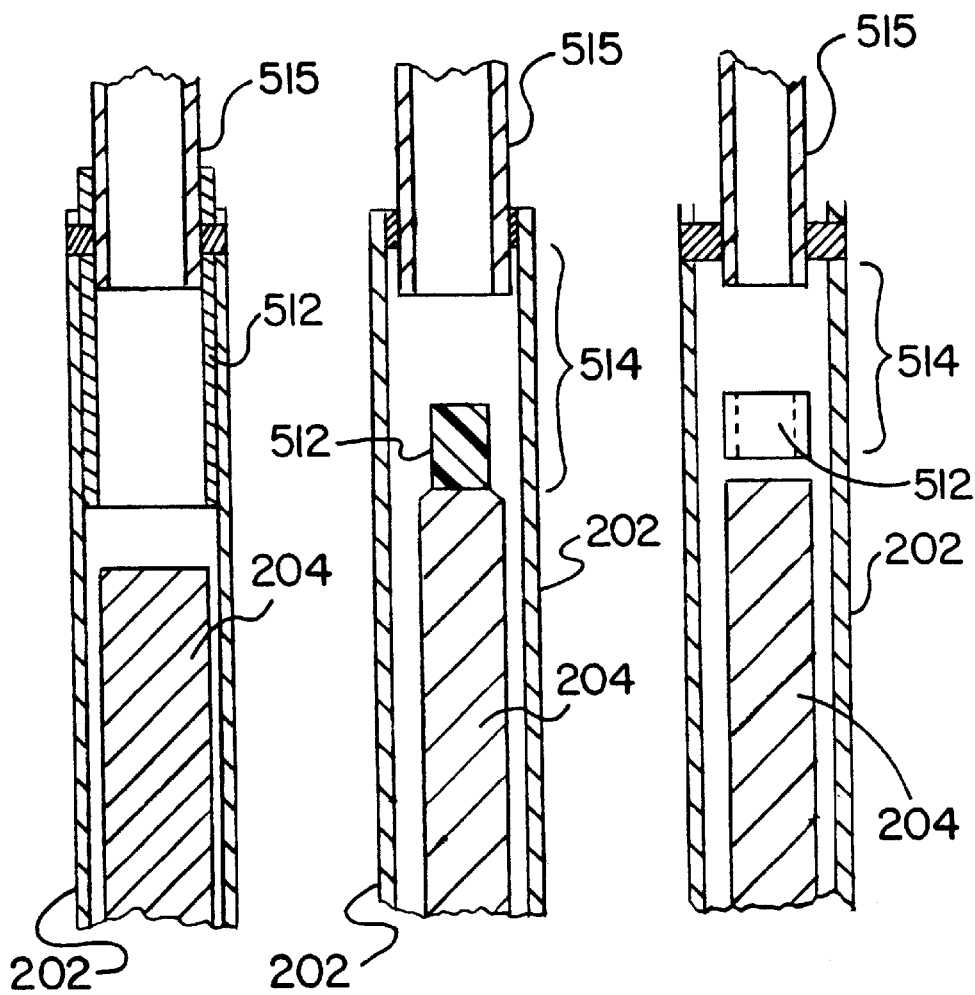
FIGS. 7A–7C illustrate cross-sections of embodiments of the containment device of the instant invention.

FIGS. 7A–7C illustrate additional ways in which a thermoplastic polymer material 512 can be placed in closure region 514 for wet sealing. Cell delivery means 515 are also provided in the figures.

Figure 8:
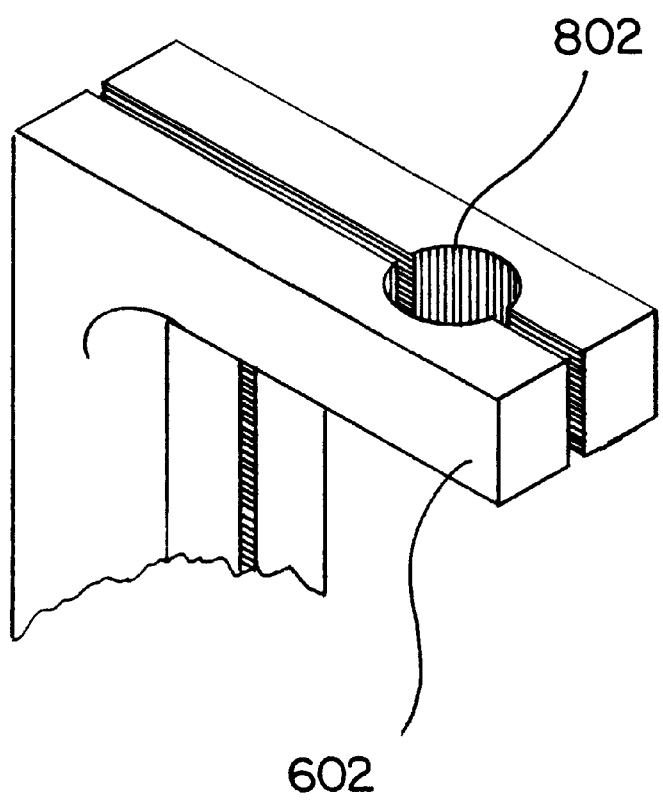
FIG. 8 illustrates an embodiment of a heat source used to form closure regions or seals in containment devices of the instant invention.

Referring to FIG. 8, the same heat device used to form closure 520 at the distal end of the containment device can be used to create seal 720. The heat device 602 is an electrically heated clamp or forceps with a cylindrical opening 802 between the clamping jaws to surround the containment device 100. The jaws are about 2–3 mm thick. This design allows application of heat around the circumference of the containment device and formation of a cell impermeable seal or closure. The heat device need not be electrically heated. For example, an ultrasonic heating device or a radio frequency induction device can be used to generate heat in the desired location and thereby melt or fuse the FEP thermoplastic.

When used in combination with a containment apparatus of the type disclosed by Butler et al. in U.S. Pat. No. 5,843,069, it is often desirable to form the sealed ends of the device into a smooth regular shape, such as a hemisphere. Applying a heated mold having the desired shape to the sealed end of the present invention is a preferred way of reshaping the sealed end. Heat can be generated in the mold with infrared energy, ultrasound, or radio frequencies.

Figure 9:
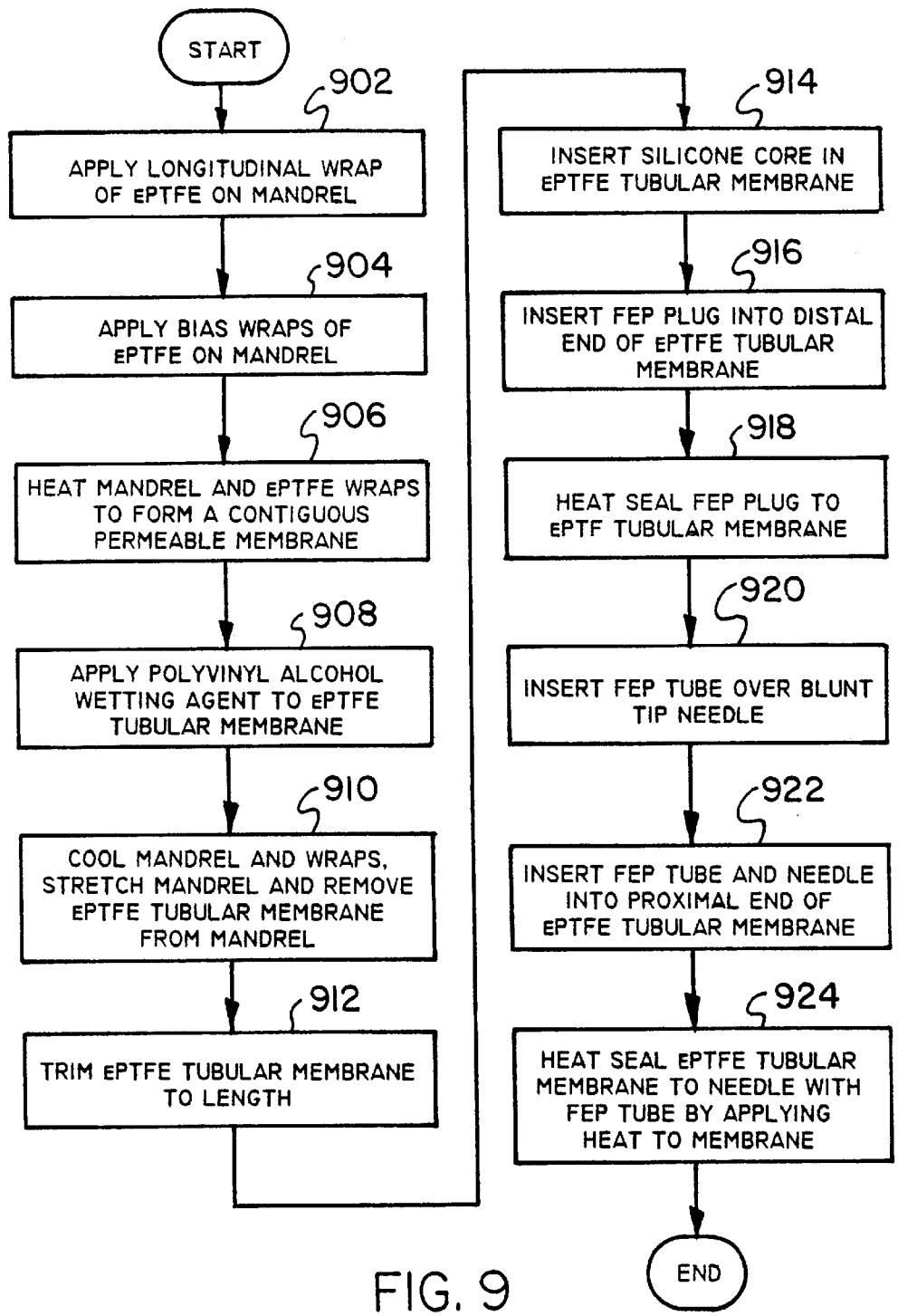
FIG. 9 illustrates an embodiment of steps to form a containment device of the instant invention.

The method of making the containment device of the instant invention has been described with reference to the figures. Referring to FIG. 9, that method is summarized as follows: At step 902, ePTFE membrane material, made in the manner described above, is applied to a silver-plated copper (SPC) mandrel that is approximately 1.5–2.5 mm in diameter, and approximately 810 mm long. The first wrap is a longitudinal wrap of 0.5 inch wide ePTFE, and provides longitudinal strength to the resulting tubular ePTFE membrane. The longitudinal wrap that is applied at step 902 is overlapped at the tape edges to form the tubular shape.

At step 904, subsequent bias or helical wraps of ePTFE are applied over the longitudinal ePTFE wrap. In a preferred embodiment, these bias wraps have about 50% overlap of the ePTFE tape. Multiple bias wraps are applied to the mandrel, with the wrap directions alternating for each successive layer. In a preferred embodiment, six (6) alternating layers of 0.5 inch wide ePTFE tape are applied to the mandrel.

At step 906, the ePTFE wrapped mandrel is placed into an oven at approximately 385° C. for approximately eight (8) minutes. This heat step allows the ePTFE wrap layers to bond, forming a tubular porous membrane. The temperature and time are selected so that the resulting bond is of sufficient strength, without loss of the desired porosity.

At step 908, the tubular ePTFE membrane is treated with a wetting agent, such as polyvinyl alcohol. This treatment helps to ensure that the normally hydrophobic ePTFE will easily wet and form a porous permeable membrane for the transfer of soluble materials.

At step 910, the tubular ePTFE membrane and mandrel are removed from the oven and cooled. The ends of the SPC mandrel are clamped, and the mandrel is stretched approximately 30%. The stretch of the mandrel necks down and slightly reduces the mandrel diameter. This reduction in diameter of the mandrel allows easy removal of the ePTFE tubular membrane from the mandrel.

At step 912, the ePTFE tubular membrane is cut or trimmed to the desired length. In one embodiment, the wrapped membrane is about 810 mm long, which is sufficient to produce four (4) individual containment devices, with an 180 mm long membrane.

At step 914, a silicone core is inserted into the trimmed ePTFE tubular membrane. The core diameter is less than the diameter of the tubular membrane, allowing the core to easily slide into the membrane. In a preferred embodiment, the core is approximately 160 mm long and the ePTFE membrane is approximately 180 mm long.

At step 916, an FEP plug, about 2 mm long, and also smaller in diameter than the ePTFE tubular membrane, is put into the distal end of the ePTFE tubular membrane. The FEP plug, silicone core and ePTFE membrane are adjusted so that only a slight length (1–2 mm) of ePTFE membrane extend beyond the FEP plug and the silicone core is close to, or abuts the FEP plug.

At step 918, the properly adjusted, or configured plug, core and membrane are heat sealed at the distal end. The heat seal is accomplished with the previously described electrically heated forceps. After heat seal, the distal end has an appearance similar to closure 520, illustrated in FIG. 7.

At step 920, an 18 gage blunt tip needle is inserted into a colored FEP tube. The inner diameter of the FEP tube is slightly less than the outer diameter of the needle, to provide a snug sliding fit.

At step 922, the combined needle and FEP tube are inserted into the proximal end of the ePTFE tubular membrane. The FEP tube is advanced into the membrane until it is about 2 mm from the end of the silicone core. This slight gap is helpful during cell loading to allow the cell suspension to flow around the silicone core.

At step 924, the properly oriented ePTFE membrane, FEP tube and needle are heat-sealed using the same electrically heated forceps to form seal 720. This is a secondary seal. After step 924, the containment device is complete and ready for sterilization and subsequent loading.

This completes the method of making the containment device. After completed, the containment device can be checked for leaks and closure integrity with any known type of leak detection, including a bubble point check. In a bubble point check, a containment device is lightly pressurized to determine if there is any leakage. An inadequate seal is revealed by the evolution of bubbles from the sealed regions of the device. The completed containment device can also be sterilized by a number of known techniques, including but not limited to chemical sterilization and steam autoclave. Steam autoclave has an advantage of wetting the membrane and displacing air within the containment device with sterile liquid.

Method of Loading the Device

A containment device 100, manufactured according to the above-described method, is preferably loaded with cell suspensions or drug formulations. As described above, an important aspect of the instant invention is the cell-impermeable nature of the device. This aspect helps to ensure that any implant cells within the containment device remain within the device. Assurance that there is no implant cell leakage from the containment device is important because the cells may be genetically engineered or not compatible with the host immune system. If the cells in the suspension can reproduce, it may be desirable to limit that reproduction to the interior of the containment device. For this reason, the cell-impermeable nature of the containment device, including the membrane and closures, is important.

The sealing mechanisms of the present invention help to ensure that contamination from implanted cells does not occur from a faulty seal in a cell containment device. In addition, the present invention also helps to ensure that contaminating implant cells do not originate from the loading system or process. This is accomplished by eliminating any open paths for the implant cells from a loading device to the exterior of the containment device during loading. This reduces or eliminates the possibility that implant cells will become attached to the containment device exterior.

Elimination or reduction in overall possibility of contamination also prevents a possibility that the implant cells can contaminate the loading area. This helps to ensure that implant cells are not inadvertently transferred from the loading area to the exterior of the containment device during routine handling.

In the present invention, one method to accomplish these objectives is to use a closed cell-tight loading system. If the implant cell loading system remains closed, there is little or no possibility that implant cells can escape from the system and contaminate the loading area or exterior of the containment device.

Figure 10:
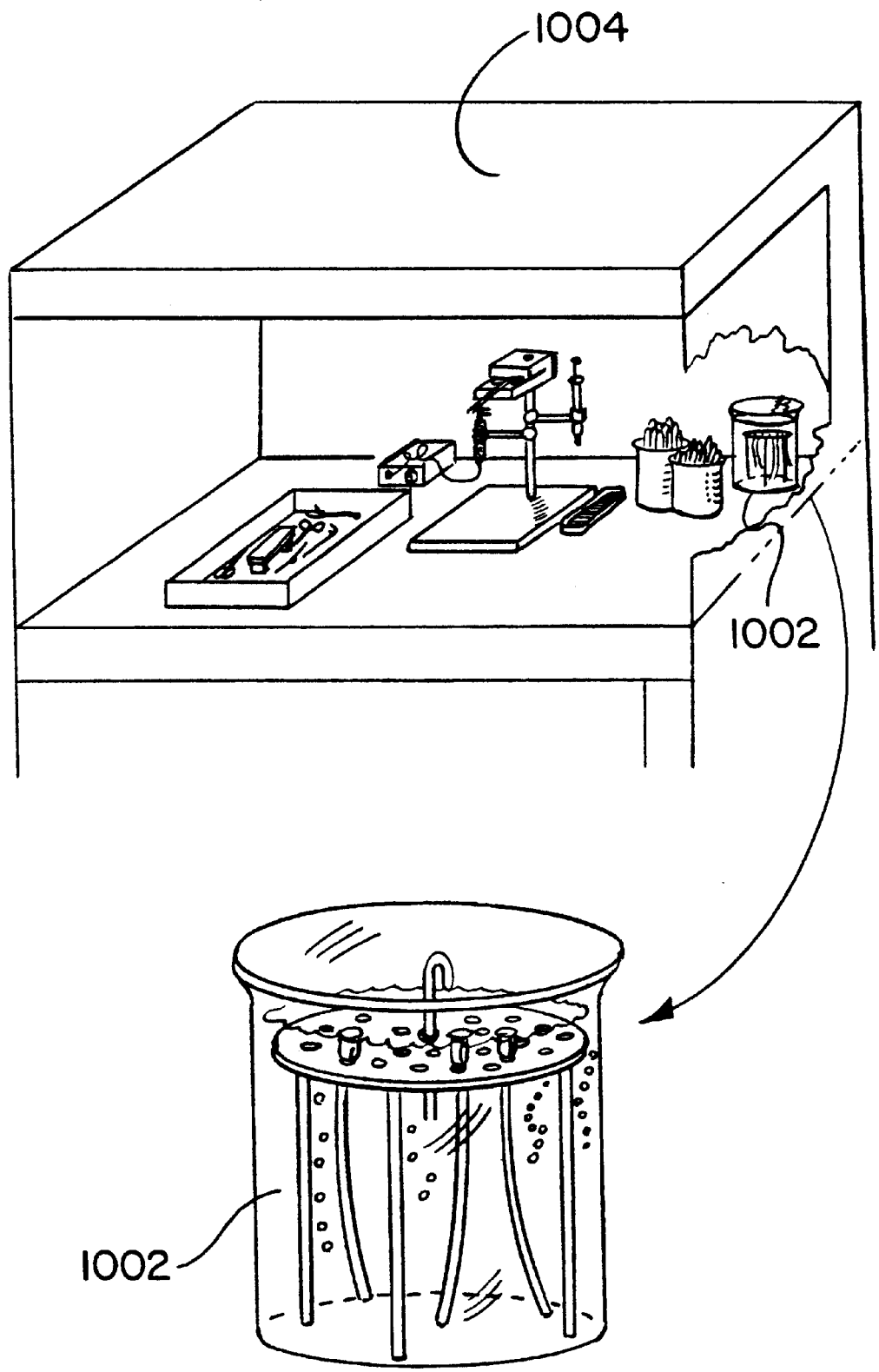
FIG. 10 illustrates a loading hood used in one embodiment for loading the containment device of the instant invention.

FIG. 10 illustrates an embodiment for manually loading containment device 100. It is understood that alternatively, the loading steps can be performed in an automated facility. When the containment device will contain a cell suspension, the empty sterilized containment device 100, immersed in sterile liquid 1002 is placed in a loading hood 1004. The equipment and tools to load and seal the containment device are also in the loading hood. Prior to placing the device in the loading hood, air is removed from the containment device and replaced by the sterile liquid. When the device is sterilized in liquid by steam sterilization, evacuation or removal of air in the device is a natural consequence of the sterilization. For other sterilization techniques that do not necessarily remove air within the containment device, an air evacuation step is generally desired.

Figure 11:
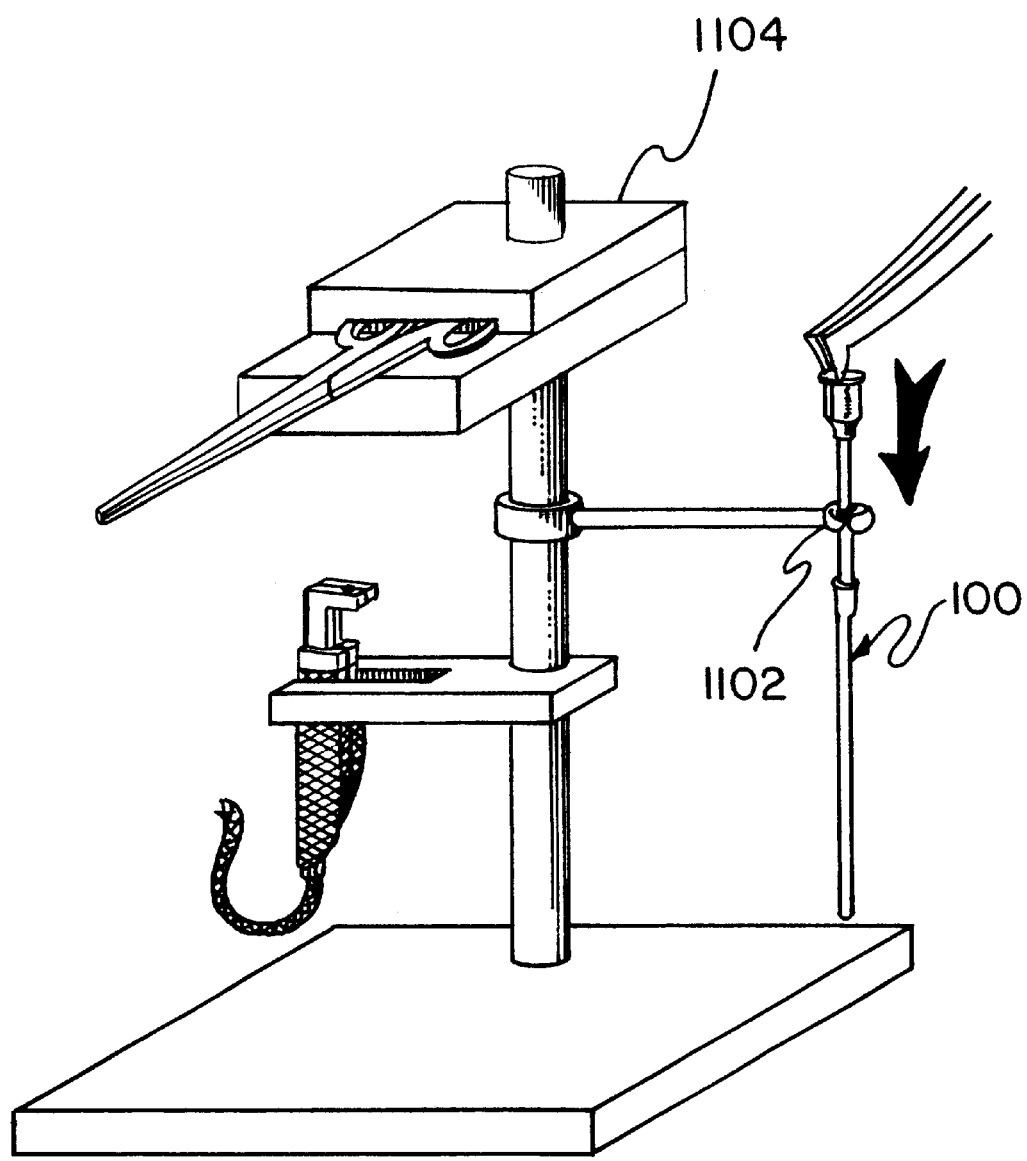
FIG. 11 illustrates a loading jig in one embodiment for loading the containment device of the instant invention.

As illustrated in FIG. 11, the containment device 100 is placed in a cell-loading fixture 1102, which is part of a loading jig 1104. This provides a stable platform for subsequent operations.

Figure 12:
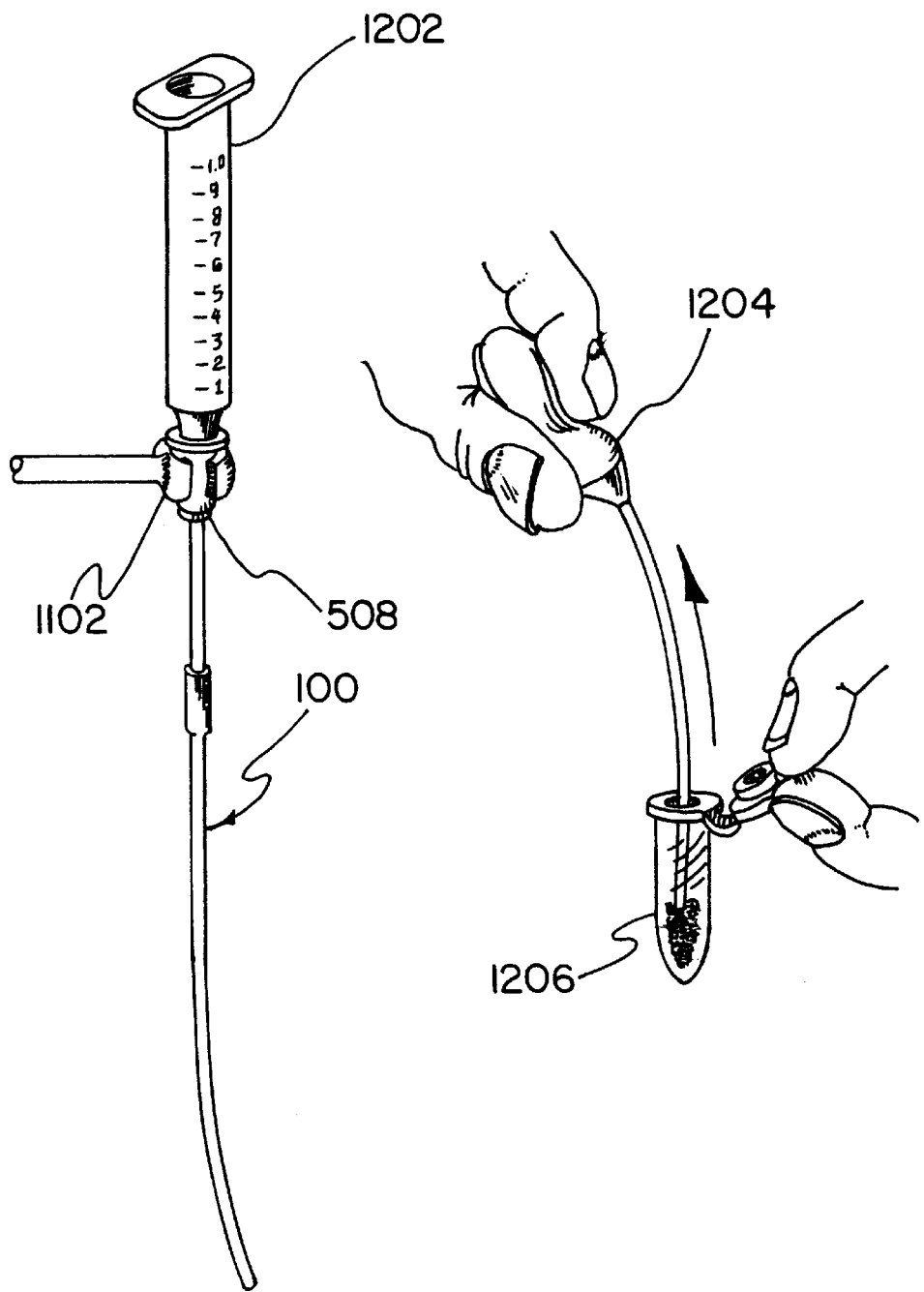
FIG. 12 illustrates an embodiment of a loading apparatus attached to a containment device of the instant invention.

Referring to FIG. 12, within the loading hood, a loading device 1202 is connected to the needle 508 of the containment device 100, such as by a luer lock. In the manual system, loading device 1202 is a 1 ml syringe. In an automated system, which is not illustrated, loading device 1202 is part of an automated cell suspension handling and delivery system. The connection between loading device 1202 and needle 508 is cell-tight. Sterile water may be present in the device and the needle and may spill onto the device at the time the two components are connected. Generally speaking, it is important that cells are not introduced into the immediate vicinity of the open needle hub 508 until the connection between the two components is first made.

When connected, devices 100 and 1202 become a closed cell-tight system. In the manual system illustrated in FIG. 12, cells in suspension are extracted with a pipette 1204 from a cell transfer container 1206.

Figure 13:
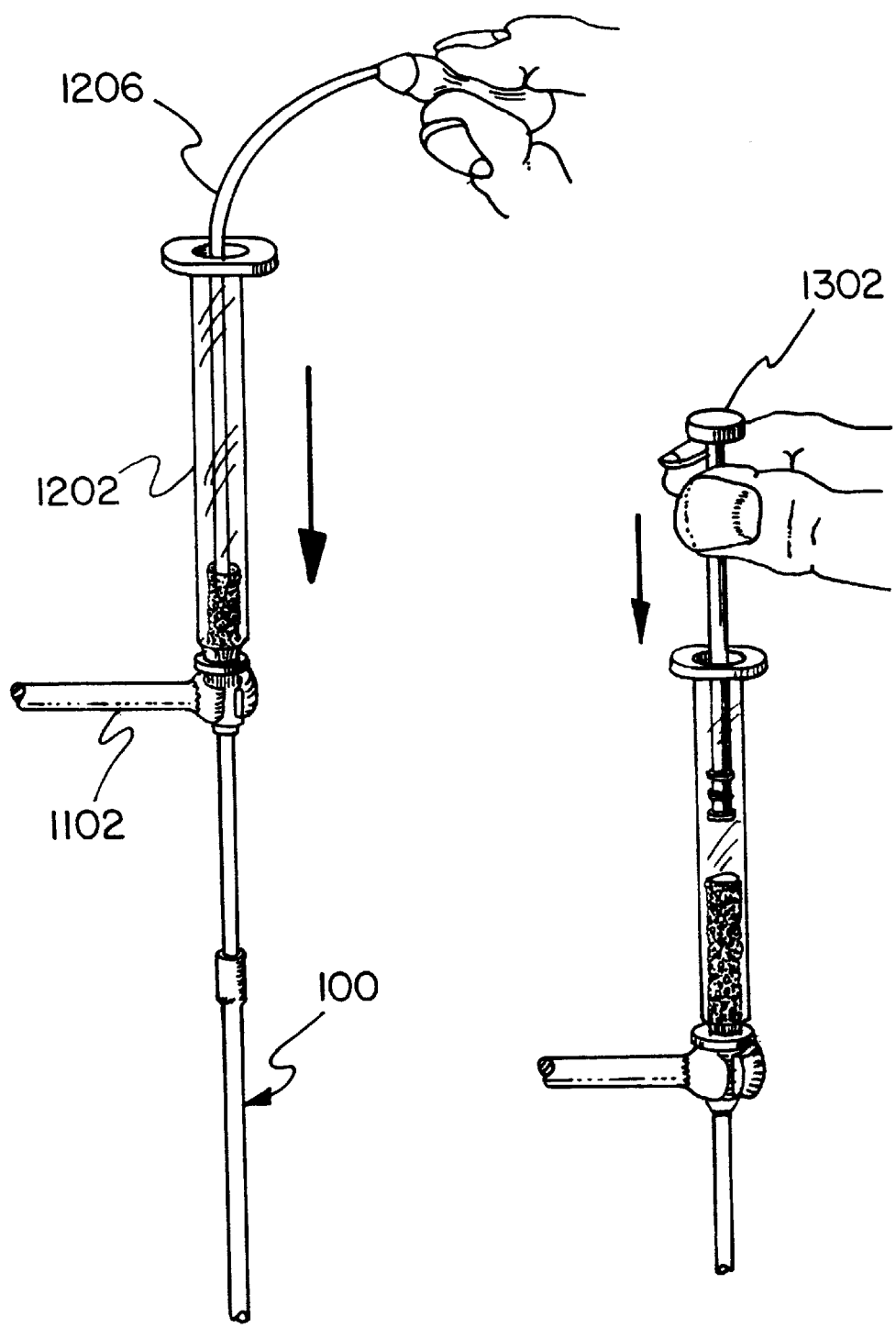
FIG. 13 illustrates an embodiment of loading cell suspension into a loading apparatus attached to a containment device of the instant invention.

Referring to FIG. 13, the pipette 1206 with cell suspension is used to place the cell suspension into the loading device 1202. It is important that cells are not allowed to leak or escape from pipette 1206 as the cell suspension is transferred. A plunger 1302 is placed into the loading device 1202, thereby closing the loading system and forming a closed cell-tight system.

Alternatively, the loading device can be charged with cells at a different station and then transported to the device loading station. Nevertheless, the cell delivery portion of the loading station is sterile at the point of contact with the containment device. The connection between the loading device and the containment device is cell-tight to ensure a closed system.

A manual loading system is illustrated in FIGS. 10–13, to clearly show the various steps for attaching the containment device 100 to the loading device 1202 and then placing a cell suspension into the loading device. However, using an open syringe, there is a remote possibility of contamination in the loading area if cells are inadvertently spilled during the pipette transfer from the cell transfer device to the loading device. Therefore, a preferred embodiment is a fully closed system, where the loading device includes suitable interlocks and valves to avoid even this remote possibility of contamination. Only after the containment device and loading device are connected, is there any loading of cells into the containment device. There is no path for cells to escape from the closed cell-tight system during loading. The only path for the cells is from the loading device to the interior of the containment device.

Alternatively, a process that permits cells to leak or escape during the loading process may be acceptable, provided the leakage is contained and isolated from the cell containment device.

Figure 14:
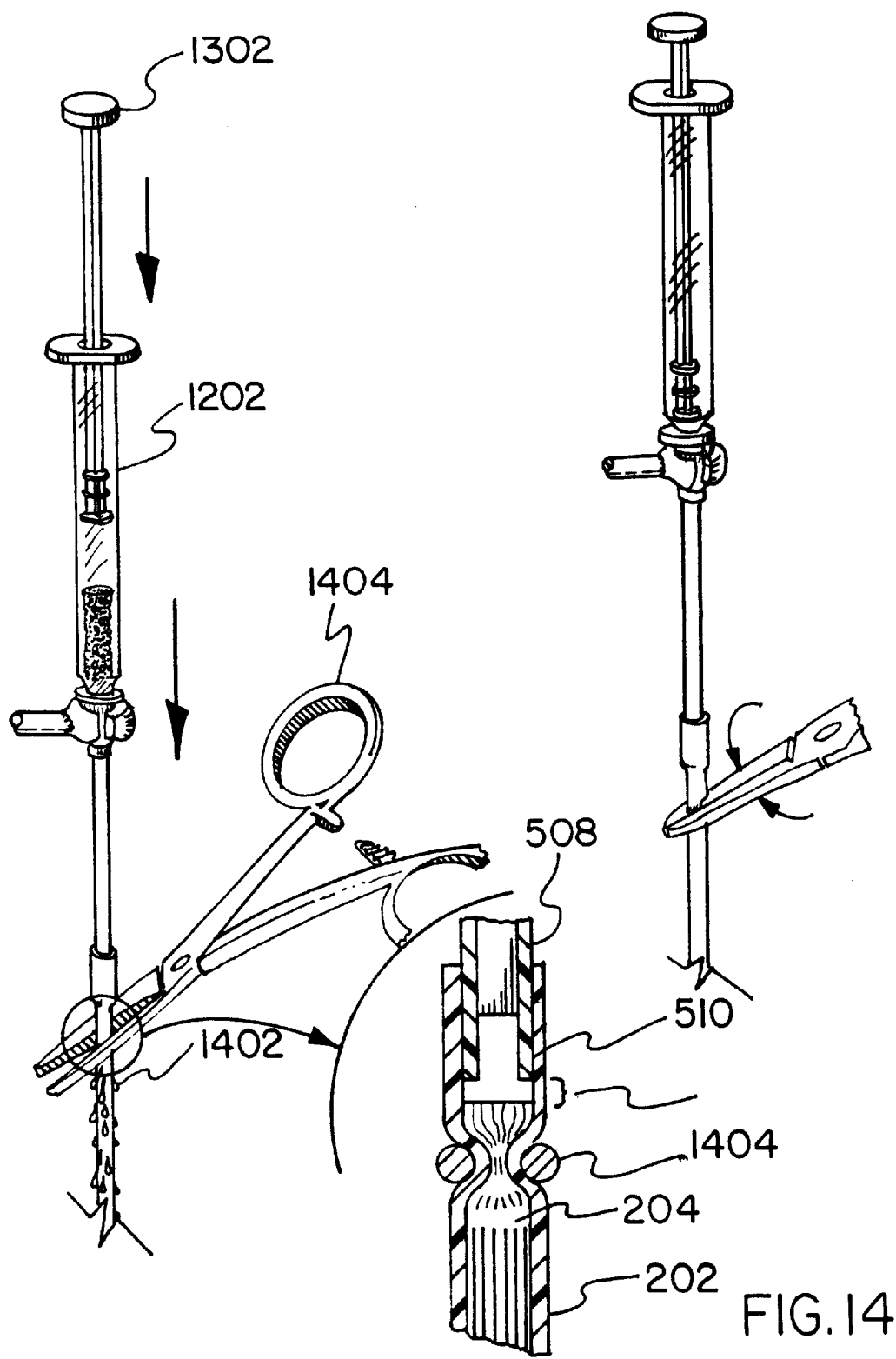
FIG. 14 illustrates an embodiment of loading cell suspension into a containment device of the instant invention and clamping the containment device after the cell suspension is loaded.

Referring to FIG. 14, after the cell suspension is within the loading device 1202, the cell suspension is loaded into containment device 100 by a slight pressure. This pressure is supplied by manually depressing plunger 1302. As the cell suspension passes into the containment device, the suspension is concentrated. This concentration is a consequence of the porous nature of the treated ePTFE tubular membrane in containment device 100. Cells are unable to pass through the membrane, but the suspension fluid is able to pass through the membrane. This serves as a sieving action by the ePTFE membrane and retains or filters the cells within the containment device, while allowing excess cell suspension fluid 1402 to pass through or weep from the ePTFE membrane of containment device 100.

Figure 21:
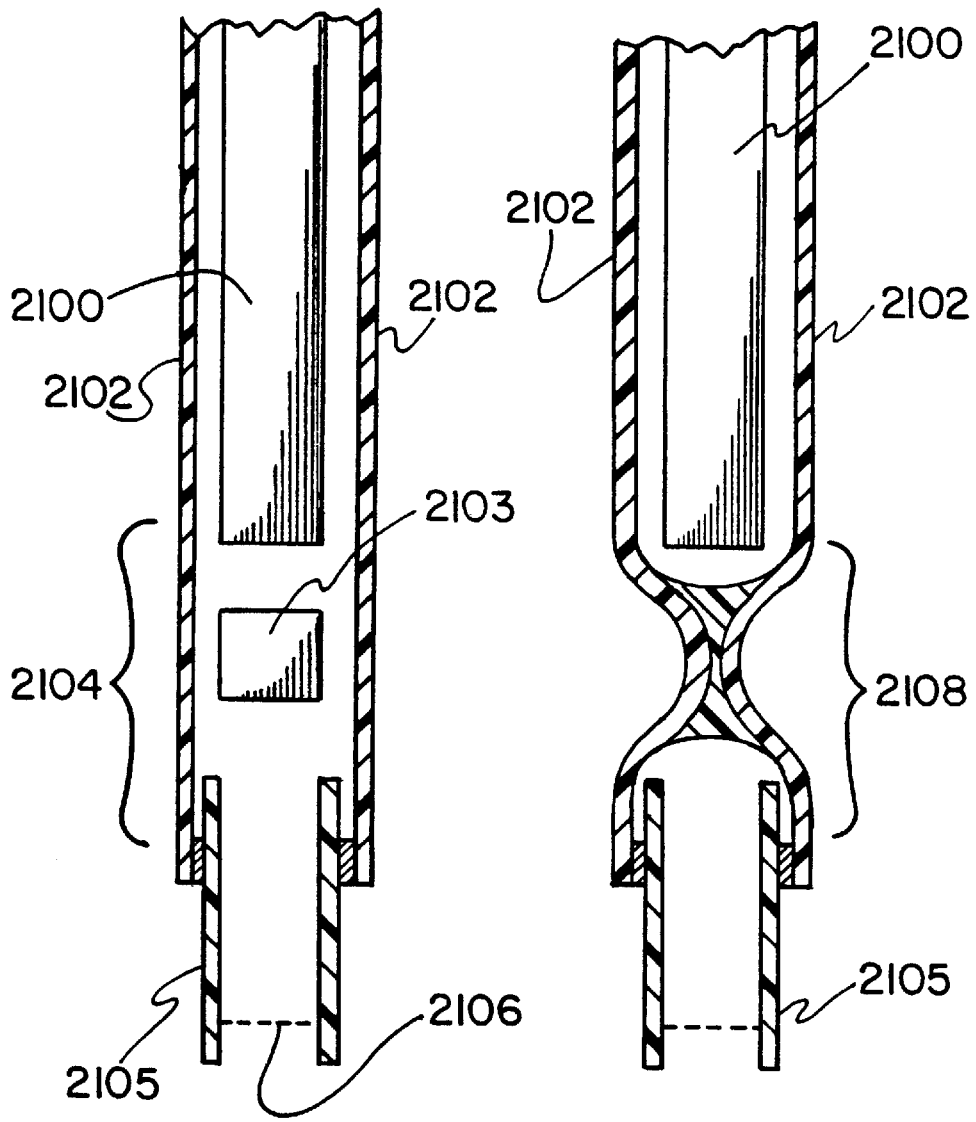
FIG. 21 illustrates an alternative embodiment of the containment device of the instant invention.

Alternatively, as illustrated in FIG. 21, if membrane 2102 does not readily permit liquid passage, end 2105 of the device is configured to act as a receptacle for receiving a fluid stream. Permeable membrane 2106 permits passage of liquids therethrough, while preventing cells from escaping the device. After the containment device is loaded, the end is then sealed 2108. This is termed a "primary seal" because the closure is formed after loading the device, while liquids of the cell suspension are contacting the membrane and sealing polymer.

Methods of Sealing the Device

Once the cell suspension is loaded into the containment device, a clamp 1404 is applied to the containment device. Preferably, the clamp is applied to a region of the tubular membrane containing the silicone core such that the very end of the core is captured by the clamping force. The clamp serves two purposes. One purpose is to serve as a heat sink during subsequent sealing operations. The other purpose is to provide a method to hold the containment device during the sealing operations.

Figure 15:
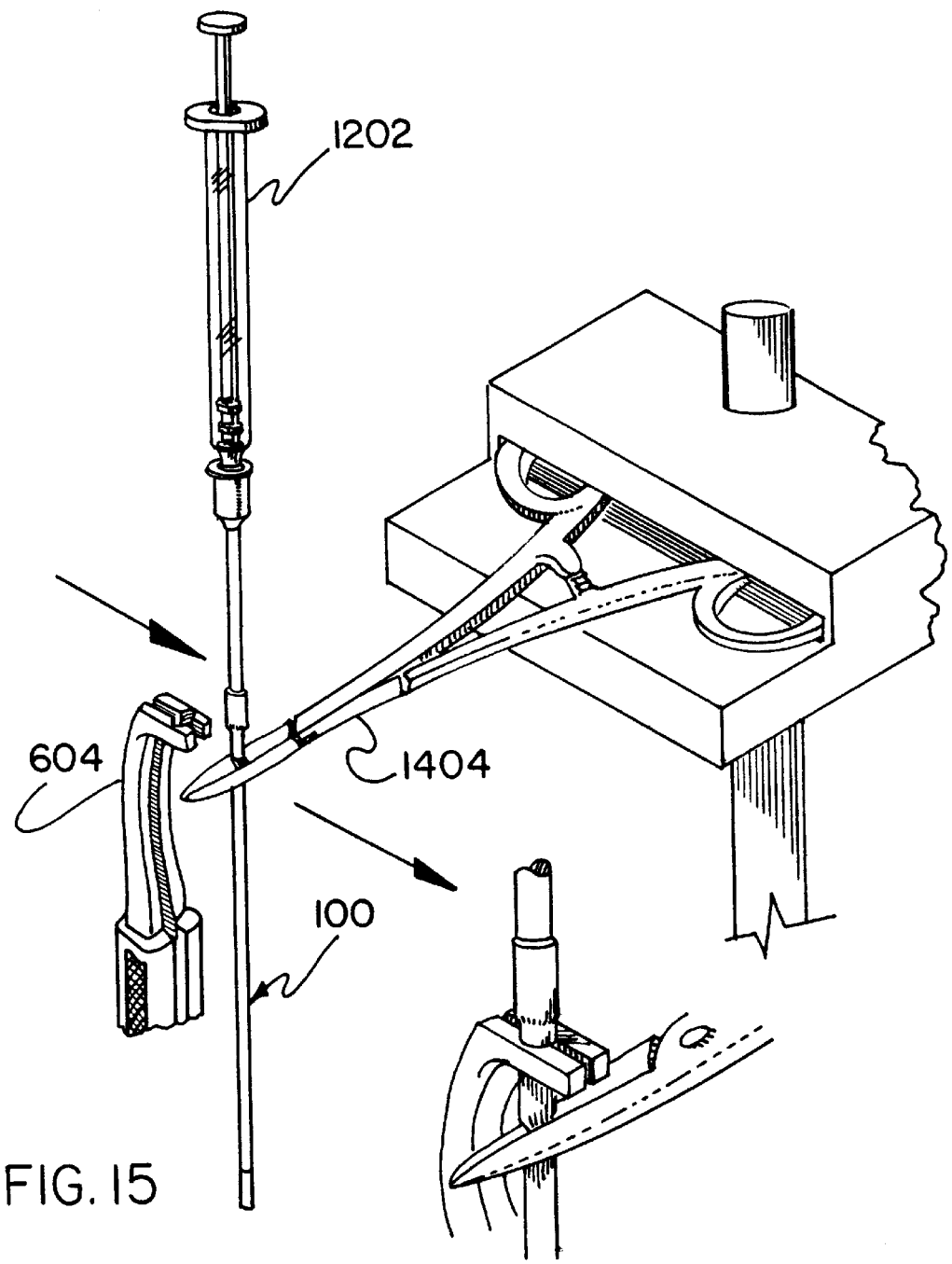
FIG. 15 illustrates an embodiment of heat sealing or closing a containment device of the instant invention using an electrically heated clamp.
Figure 16:
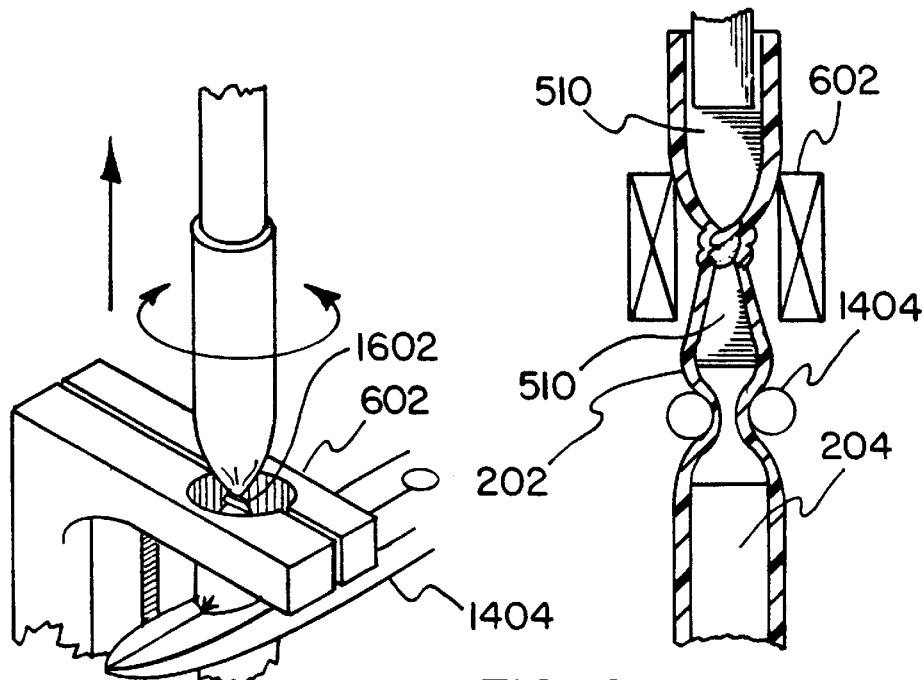
FIG. 16 illustrates an embodiment of twisting and elongating the closure region of the containment device of the instant invention.

After the cells are loaded, the system remains a closed cell-tight system during closure or wet-sealing of the containment device. Referring to FIGS. 15 and 16, heat source 604 is applied with a slight pressure to a portion of the ePTFE membrane 202 in the containment device 100 that is in communication with the FEP polymer tube 510. During heating, the device is simultaneously twisted and elongated to form a closure region 1602. Ideally, the twist is about 360 degrees, but any twist of greater than about 45 degrees helps to accomplish the objective of constricting and compressing the closure.

The twisting and elongation serves to provide a visible separation region. The elongation also ensures that when the containment device is separated from the needle and loading device, a seal or closure remains on each side of the separation. This wet-seal in closure region 1602 is termed a primary seal.

The heating serves to cauterize the closure and kill any cells that may be within closure region 1602. The elongation and twisting also provides a slight pressure in the area of the closure and serves to provide a visible separation region. The elongation also ensures that when the containment device is separated from the needle and loading device, a seal or closure remains on each side of the separation, thereby ensuring that the system remains a closed cell-tight system; cell leakage is prevented from the closure. In a preferred embodiment, this elongation and closure is about 2 mm long, which can be visibly observed and readily bisected.

After the closure is created by heating, elongation, and twisting, the closure is allowed to cool. At this point, the containment device with the loaded cells or drugs remains attached to the needle by the closure. However, the closure eliminates any fluid passage between the needle and the containment device. This can be verified by slightly pressurizing the needle side of the closure and ensuring that no additional weep emerges from the containment device. With an integral closure, the containment device can be separated from the needle, without any fear of cell leakage from either the containment device, or the loading device. Any cells within the closure region were either killed outright by the heat closure, or rendered metabolically non-functional. The only step remaining in the seal or closure step is to separate the containment device from the needle.

Figure 17:
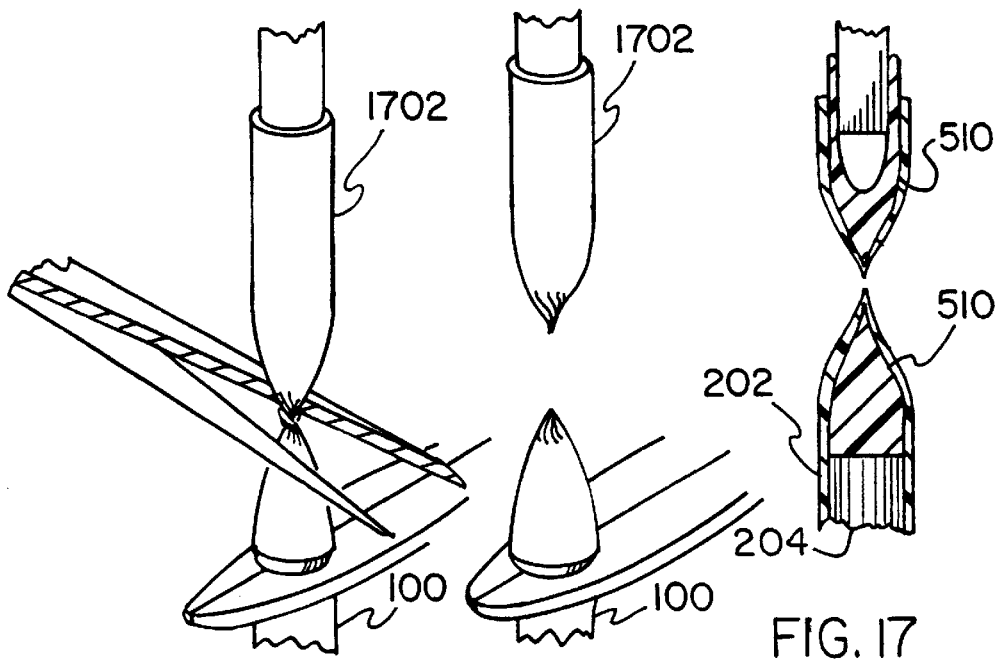
FIG. 17 illustrates an embodiment of separating the sealed containment device of the instant invention from the loading apparatus, and the resulting closure at the closure region.

Referring to FIG. 17, after the closure is formed, the containment device 100 is separated from the needle elements 1702. Separation is performed with scissors or a knife. Care is taken to make the separation in the middle of the closure region, thereby maintaining cell-tight seals after the separation. The resulting closure on containment device 100 and needle elements 1702 include a fused or welded area with FEP 510 and ePTFE 202.

The subsequent processing includes disposal of needle elements 1702 and other associated elements of the loading device.

If the closure of the containment device extends, it may be appropriate to trim excess material from the closure. This is important if the excess material can contact the containment apparatus during placement or replacement of the containment device.

The primary seal just described is formed as a wet seal, because it is formed in a containment device that has been loaded with a cell suspension, resulting in a wet membrane.

Even after the containment device is sealed or closed and separated or cut from the loading device, the system remains closed. The closure substantially or completely seals the closure region and the heat used to create the closure helps to ensure that any cells within the closure region are either killed, or have their metabolic capabilities destroyed. This ensures that cells are not released into the loading area or sterile field, and also helps ensure that multiple cell loads can be performed without risk of contamination from previous loading operations.

In the described embodiment, heat from an electrically heated clamp is used to form the closures. In other embodiments, the closure of the containment device is created by other forms of heat application, such as ultrasonic welding or radio frequency inductive heating. The only requirement for heat closure is that the heat be applied locally in the closure region, and that it melt the thermoplastic polymer to allow formation of the closure, without compromising the integrity of the ePTFE membrane.

In another embodiment, the closure of the containment device is created by heating only the membrane material, without any thermoplastic. The only requirement is that the resulting closure provide the required degree of closure or cell-impermeability.

Figures 19A, 19C:
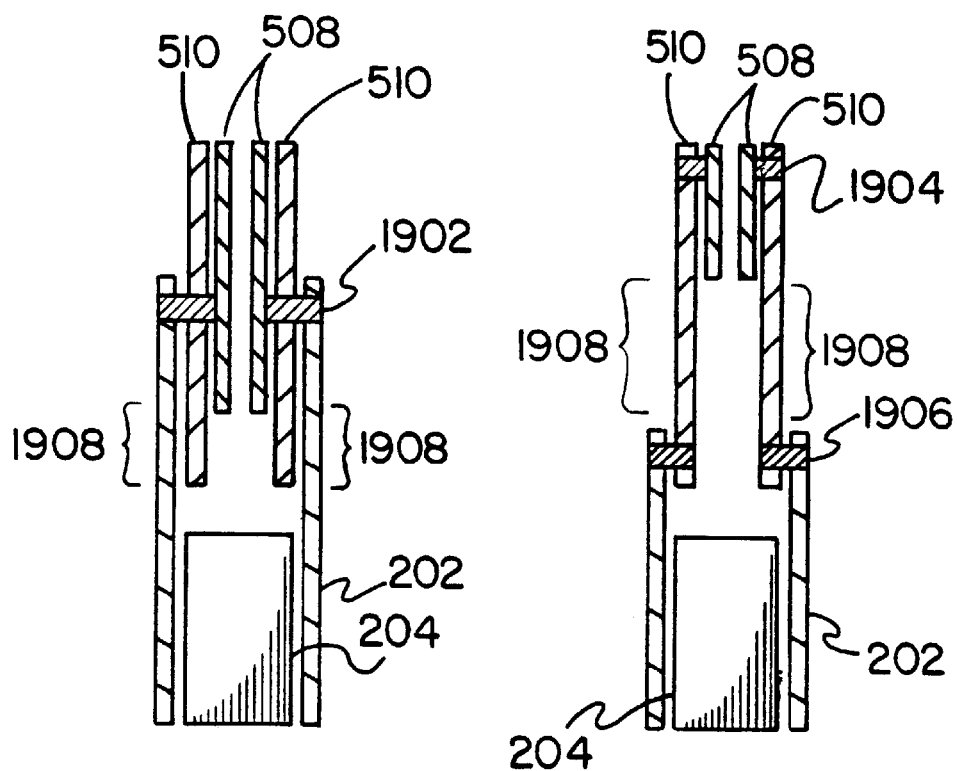
FIGS. 19A–19C illustrates alternative embodiments of the containment device of the instant invention.

In another embodiment, a closure is formed by heating only a thermoplastic material previously attached to the permeable membrane material. As shown in FIG. 19C, the closure is made with a thermoplastic material having a portion is attached to the permeable membrane and a portion that extends beyond the permeable membrane to provide a port made solely of thermoplastic material.

In another embodiment, the closure at the end of the containment device that is normally created by a dry seal (i.e., the distal end) before the device is loaded, is created by a wet seal technique. In this embodiment, the membrane is wet when the closure at the distal end is created. The source of the wet membrane is not limiting and may be the result of a cell suspension load, a drug load, a wetting agent or a sterile solution.

The closure can also be created by non-heat methods, such as solvents or chemicals. In this embodiment, an important aspect of the closure is that after the closure is formed, there is little or no possibility that living or viable cells remaining within the closure region. If the solvent or chemical is toxic to the cells, then formation of the closure itself may be sufficient to ensure that the closure region is free of viable cells. However, if the solvent or chemical is not toxic to the cells, then an additional step must be provided to ensure that any cells within the closure region are killed or rendered non-metabolically functioning. For example, it may be appropriate to use an ultraviolet light cured or activated compound or glue to create the closure. These compounds or glue may not be toxic by themselves, but the UV cure may be sufficient to render the closure region cell dead or metabolically functioning.

Figure 18:
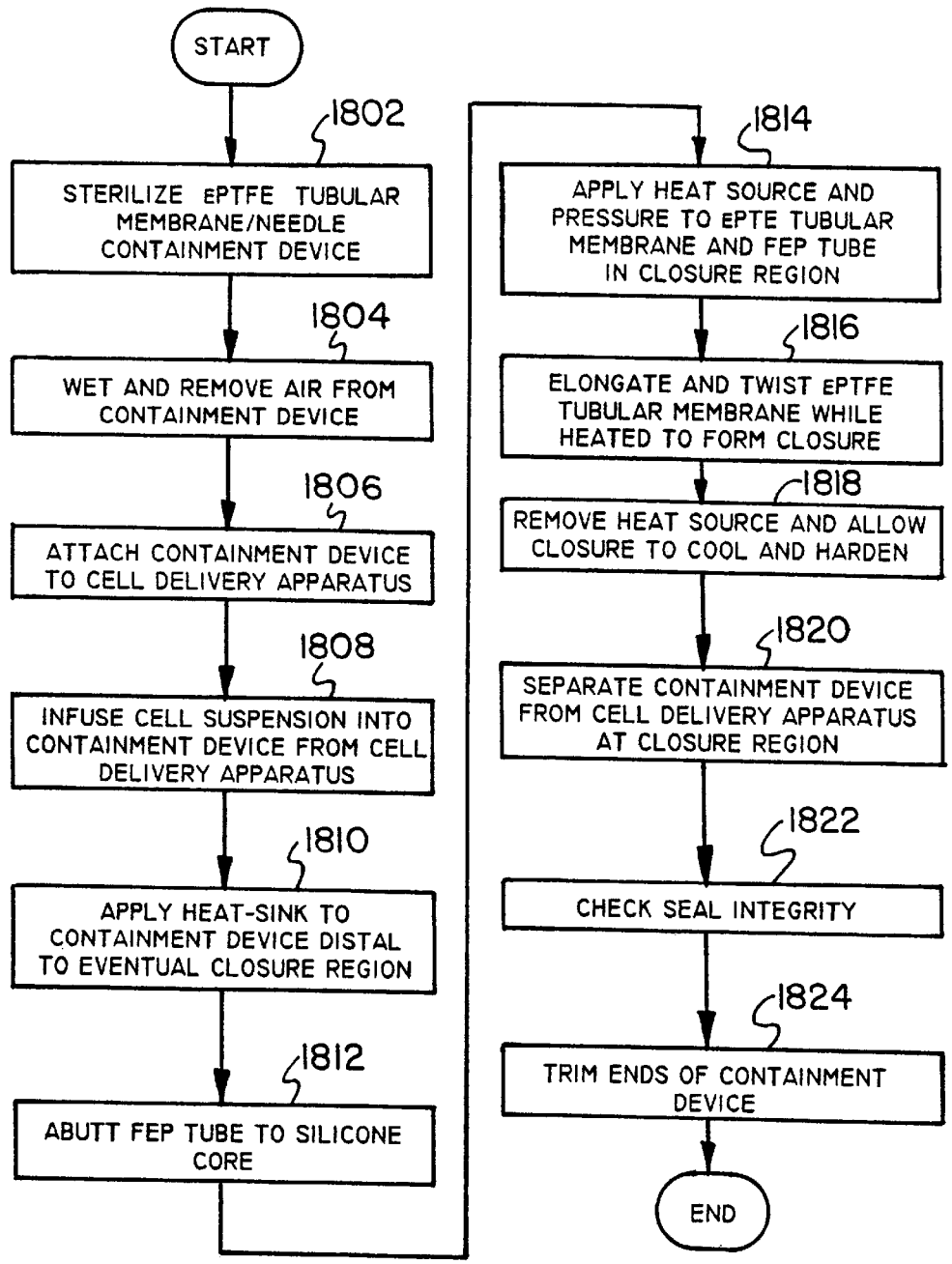
FIG. 18 illustrates an embodiment of steps to close or seal a containment device of the instant invention.

The method of filling and sealing the containment device of the instant invention has been described above with reference to the figures. Referring to FIG. 18, the steps of filling and sealing are summarized. At step 1802, the ePTFE tubular membrane and needle containment device is sterilized. As indicated above, this is with any of a number of different techniques, though steam sterilization is preferred as initially wetting the membrane of the device.

At step 1804, air is removed from the containment device and the membrane is wet, if not accomplished in the sterilization step.

At step 1806, the containment device is attached to the cell delivery apparatus.

At step 1807, a cell suspension is transferred to the cell delivery apparatus.

At step 1808, a closed cell-tight system is formed.

At step 1809, a cell suspension is infused into the containment device from the cell delivery apparatus. During this step, the cell suspension can be concentrated, as the membrane serves as a sieve to allow excess suspension fluid to weep from the containment device membrane.

At step 1810, after the cell suspension is infused, a heat sink is applied to the containment device. The heat sink is positioned just distal to the eventual closure region.

At step 1812, the FEP tube is moved within the membrane so as to abutt the silicone core. As discussed above, there is a gap between the silicone core and the FEP tube to assist with cell loading. Prior to sealing the containment device, this gap is preferably closed at step 1812.

At step 1814, a heat source is applied to the ePTFE tubular membrane in the vicinity of the closure region. The heat source is any of a number of different types, with an electrically heated forceps a preferred embodiment.

At step 1816, while the heat source is maintained near the closure region, the ePTFE membrane is both elongated and twisted to form the closure. This combination of actions applies pressure in the vicinity of the closure and helps to ensure a good seal. The heat, elongation and twisting provides a cell kill zone. It is possible that the ePTFE membrane is only twisted, or only elongated to create the closure. However, a combination provides the best closure.

At step 1818, the membrane closure is allowed to cool after removing the heat source. As the FEP and ePTFE cools, it hardens to form the closure.

At step 1820, the containment device is separated from the cell delivery apparatus at the closure region. This is accomplished by cutting at the mid-point of the closure with a scissors or knife.

At step 1822, integrity of the seal at the cell delivery apparatus is checked, such as by slightly pressurizing the apparatus and observing any leaks.

At step 1824, ends of the containment device are trimmed to remove any irregularity or sharp features which might be problems during subsequent implant.

At this point, the containment device has been loaded with a cell suspension, and the device has been sealed to form a cell-impermeable region at the closure regions. The only steps remaining are preparation for implant and implantation of the containment device directly into a recipient or indirectly in an implantable containment apparatus.

In the previous description, one embodiment and configuration of the containment device has been used to illustrate the inventive aspects. FIG. 19 illustrates another embodiment of the instant invention. In FIG. 19A, the tubular membrane 202, FEP tube 510 and needle 508 are configured as generally described above. When the containment device is made, heat is applied to the ePTFE membrane, causing the FEP and membrane to fuse or melt and thereby create a seal 1902 with needle 508.

Figure 19B:
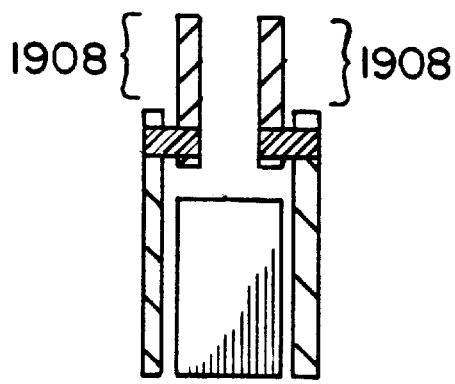

In another embodiment, illustrated in FIGS. 19B and 19C, the membrane is sealed to the FEP tube. However, the membrane does not extend into the closure region and the closure is created with only FEP. The FEP may be further connected in a cell-tight fashion, to other cell delivery components (see FIG. 19C). Cell-tight methods of connection include heat welds, luer locking, etc.

In an embodiment illustrated in FIG. 19C, the tubular membrane 202 is heat sealed to FEP tube 510, to form seal 1906. However, membrane 202 is not directly sealed to needle 508. In the embodiment illustrated in FIG. 19C, FEP tube 510 is heat sealed to needle 508 to form secondary seal 1904. As illustrated in FIG. 19C, an additional seal is made during containment device manufacture. In the subsequent loading of the containment device, it is clear that a closure in seal region 1906 will include both ePTFE and FEP. However, a closure in seal region 1908 will include only FEP. Depending on a number of factors, it may be desireable to use the embodiment illustrated in FIG. 19A for some applications, and the embodiments illustrated in FIGS. 19B and 19C for other applications.

Figure 20:
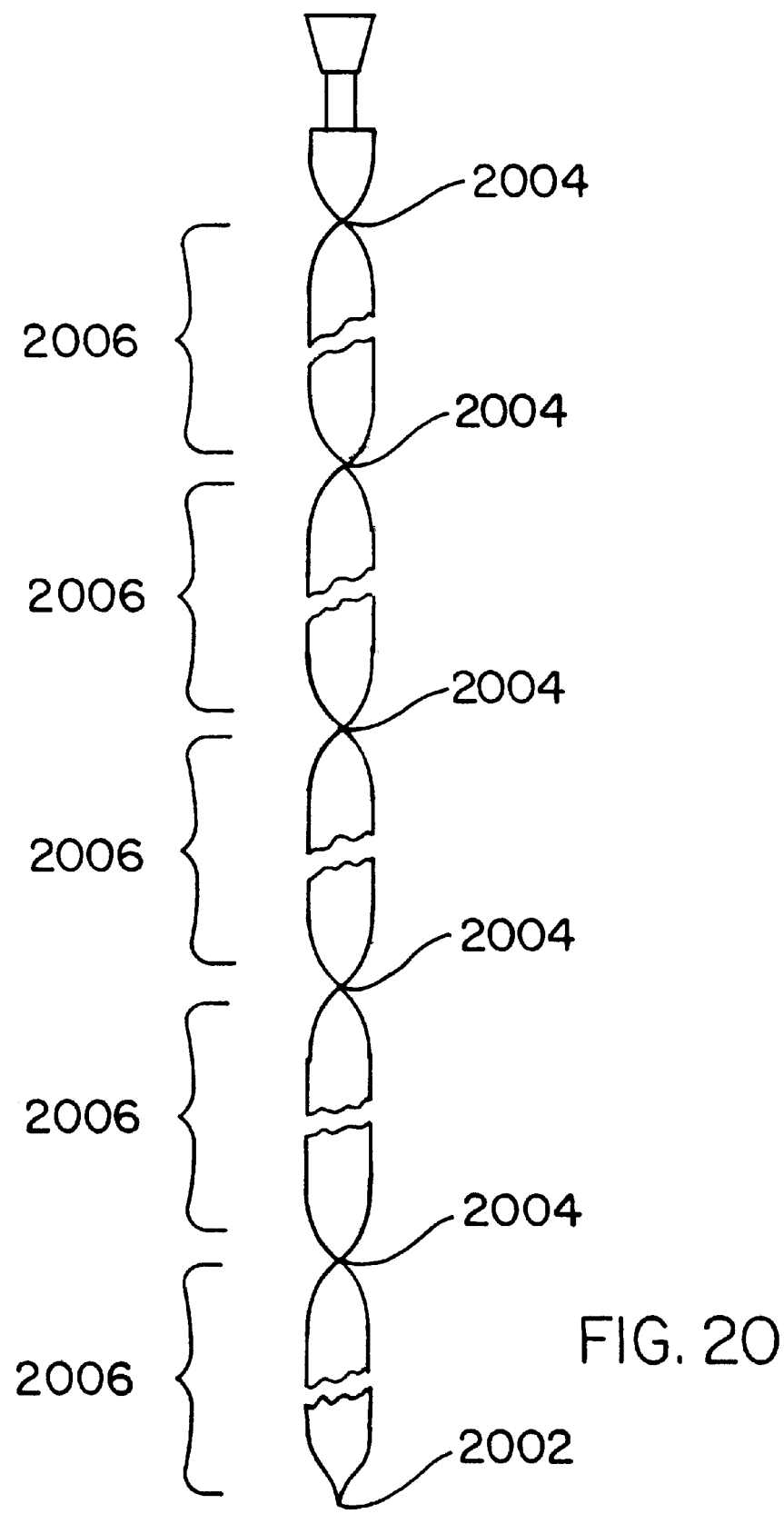
FIG. 20 illustrates an alternative embodiment of the containment device of the instant invention.

FIG. 20 illustrates an alternative embodiment where a wet or dry seal 2002 is formed on the end of a string or "sausage-link" of multiple containment devices 2006. The devices are simultaneously loaded and individual closures 2004 are formed between devices 2006. The individual devices are then separated at the closures 2004 between the devices 2006. This has an advantage of volume processing.

FIG. 21 illustrates an alternative embodiment, which is particularly advantageous where membrane weeping is not desired or possible. In this embodiment, membrane 2102 surrounds core 2100. An FEP plug 2103 is between core 2100 and terminal 2105. Terminal 2105 is connected to membrane 2102 and is either a filter 2106, to allow concentration of a cell suspension as described above, or a fluid receptacle (not illustrated) to capture cell or drug suspension after flow through the containment device. A wet seal is effected in closure region 2014.

After loading with the drug or cell suspension, a closure 2108 is formed in one of the manners described above for other embodiments. In this manner, the containment device can be readily loaded even when membrane 2102 does not or cannot weep.

It is also apparent, though not illustrated, that the tubular membrane need not be outside the FEP tube. For example, the needle might be inserted into the tubular membrane and the FEP tube placed over both the membrane and needle.

Clinical Testing

Clinical success with any implantable device containing somatic cells, engineered somatic cells, or immortalized transformed cells must contain those transplanted cells for the life of the device. Many of the proposed populations of cells to be used for somatic cell therapy in the instant invention are both motile and immortal. Keeping those migratory cell populations within the device is a critical design parameter.

In vitro load testing was conducted in order to rigorously measure the ability to load containment devices of the present invention without any external cell contamination. Possible sources of cell contamination on external surfaces of the devices include cells being ultra-filtrated through the ePTFE membranes, back washed out the proximal end of the device before the wet seal is done, pinholes, or simply erroneous external contamination of the devices during the load procedure. Prokaryotic cells were used in the tests rather than mammalian cells because of their much smaller size and much faster growth rates. Use of prokaryotic cells is believed to be a valid and extremely sensitive measure of external contamination from any source during loading of the device.

Cell containment devices having wet seals were made as described above and presented with a bacterial challenge by loading broth cultures containing either of two types of bacteria, *M. luteus* or *P. aeruginosa*, into the devices. These organisms were chosen due to size, shape and motility differences that might affect their ability to be ultrafiltrated and/or migrate through the ePTFE membranes of the present invention. Also, the colony growth and broth culture characteristics allow easy and quick identification of each type of organism.

During loading, the fluid that normally ultra-filters through the permeable membrane of a containment device of the present invention was aseptically collected drop by drop onto standard microbiologic culture plates of tryptic soy agar (TSA). The bottoms of the plates were marked indicating the exact location of where each drop fell. Once the devices were filled with the particular bacteria and the ultrafiltrate samples collected and marked, the devices were wet sealed and placed into broth culture at 37 degree's centigrade along with their respective culture plates (ultrafiltrate samples). The ultrafiltrate collected from the loading of the test devices were negative for growth of both organisms tested. No colonies were present on the agar plates in the regions marked to indicate where the ultrafiltrate drops landed on the agar.

When cell-permissive devices (i.e., intentionally made leaky) were loaded with either *M. luteus* or *P. aeruginosa* and the ultrafiltrate collected onto sterile agar plates, there was rapid colony growth in exactly the spots where the drops of ultrafiltrate landed. The colony color (*M. luteus* is yellow) and morphology was consistent with the original two organisms used and not a contaminant. In addition, the colonies were sampled and sent out for identification. The external results confirmed the identifications as Pseudomonas spp. or Micrococcus spp.

Further studies were conducted by placing test devices and control devices in an in vitro culture. Test devices for this study were intentionally made to leak bacteria. Control devices were made according to the teachings of the present invention and were not made to leak bacteria. Following loading of the devices with one of the two strains of bacteria, the test and control devices were placed into a tryptic soy broth (TSB) for culture. If a wet sealed containment device is not cell-tight, bacteria escape the device and bloom into a turbid culture within a matter of hours. The TSB media around the test devices became turbid within a matter of hours for both species of bacteria tested. In contrast, the culture media in which the control devices were cultured showed no turbidity.

Although illustrative embodiments have been described herein in detail, it should be noted and will be appreciated by those skilled in the art that numerous variations may be made within the scope of this invention without departing from the principle of this invention and without sacrificing its chief advantages.

Unless otherwise specifically stated, the terms and expressions have been used herein as terms of description and not terms of limitation. There is no intention to use the terms or expressions to exclude any equivalents of features shown and described or portions thereof and this invention should be defined in accordance with the claims that follow.

We claim:

1. A method of closing a cell containment device comprising:
   providing a cell containment device comprising a permeable membrane made of a fluoropolymer, said permeable membrane delimiting a space for containing cells therein, a closure region comprising a thermoplastic polymer in association with the permeable membrane and means for placing cells in said space through said closure region, wherein said closure region is closeable with a cell-tight seal formed in the presence of an aqueous liquid;
   wetting said permeable membrane and said thermoplastic polymer with an aqueous liquid; and
   applying sufficient heat to at least one portion of said wetted thermoplastic polymer to cause said wetted thermoplastic polymer to melt and flow along surfaces and into available interstices of the permeable membrane to create at least one cell-tight seal and provide a cell containment device suitable for use as a medical device.

2. A method according to claim 1, further comprising applying a heat sink to said membrane before said applying heat.

3. A method according to claim 1, further comprising checking closure integrity after said applying heat.

4. A method according to claim 1, further comprising cutting said closure.

5. A method according to claim 1, further comprising trimming excess membrane from said containment device after said applying heat.

6. A method according to claim 1, further comprising applying pressure to create the closure.

7. A method according to claim 1, wherein the membrane is tubular, said method further comprising creating a closure on a first end of the tube, loading cells into said space, and wet sealing a second end of said tube.

8. A method according to claim 7, wherein said closure on a first end is created with a dry seal technique.

9. A method according to claim 7, wherein said closure on a first end is created with a wet seal technique.

10. A method according to claim 1, wherein applying heat includes applying infrared energy.

11. A method according to claim 1, wherein applying heat includes applying ultrasonic energy.

12. A method according to claim 1, wherein applying heat includes applying radio frequency inductive energy.

13. A method according to claim 1, wherein wetting includes placing a cell suspension into said space delimited by said membrane.

14. A method according to claim 1, wherein wetting includes placing a drug formulation into said space delimited by said membrane.

15. A method according to claim 1, wherein applying heat includes applying heat above a melt point of said thermoplastic polymer.

16. A method according to claim 1, further comprising elongating said membrane while heating or twisting said membrane.

17. A method according to claim 16, wherein the elongating includes elongation of greater than one percent.

18. A method according to claim 16, wherein the twisting includes twisting of greater than 45 degrees.

19. A method according to claim 16, wherein the twisting provides a separation region.

20. A method according to claim 1, further comprising separating the containment device into a first device and a second device.

21. A method according to claim 20, wherein the first device is a containment device.

22. A method according to claim 20, wherein the second device is not a containment device.

23. A method according to claim 20, wherein the first and second device are both containment devices.

24. A method according to claim 1, wherein the membrane includes FEP in association with the membrane, the FEP forming part of the closure after said heating and twisting.

25. A method according to claim 1, wherein the closure is approximately 2 mm in length.

26. A method according to claim 1, wherein the membrane includes PTFE.

27. A method according to claim 1, wherein the thermoplastic polymer includes FEP.

28. A method according to claim 1, wherein the thermoplastic polymer has a color that is distinct from a color of the permeable membrane.

29. A method according to claim 1, wherein the permeable membrane substantially surrounds the thermoplastic polymer.

* * * * *